United States Patent
Zhang

(10) Patent No.: US 12,329,942 B2
(45) Date of Patent: Jun. 17, 2025

(54) INJECTION HEAD OF NEEDLELESS SYRINGE, NEEDLELESS SYRINGE BODY AND NEEDLELESS SYRINGE

(71) Applicant: BEIJING QS MEDICAL TECHNOLOGY CO., LTD., Beijing (CN)

(72) Inventor: Ming Zhang, Beijing (CN)

(73) Assignee: BEIJING QS MEDICAL TECHNOLOGY CO., LTD., Beijing (CN)

( * ) Notice: Subject to any disclaimer, the term of this patent is extended or adjusted under 35 U.S.C. 154(b) by 1099 days.

(21) Appl. No.: 17/285,749

(22) PCT Filed: Nov. 10, 2020

(86) PCT No.: PCT/CN2020/127824
§ 371 (c)(1),
(2) Date: Apr. 15, 2021

(87) PCT Pub. No.: WO2021/218108
PCT Pub. Date: Nov. 4, 2021

(65) Prior Publication Data
US 2023/0136095 A1     May 4, 2023

(30) Foreign Application Priority Data

Apr. 30, 2020   (CN) .......................... 202010366995.9
Apr. 30, 2020   (CN) .......................... 202010367033.5

(51) Int. Cl.
*A61M 5/30*     (2006.01)
*A61M 5/31*     (2006.01)
*A61M 5/315*    (2006.01)

(52) U.S. Cl.
CPC .......... *A61M 5/30* (2013.01); *A61M 5/31515* (2013.01); *A61M 2005/3128* (2013.01)

(58) Field of Classification Search
CPC ................ A61M 5/30; A61M 5/31515; A61M 2005/2403
See application file for complete search history.

(56) References Cited

U.S. PATENT DOCUMENTS 4,913,699 A   4/1990 Parsons
4,916,399 A   4/1990 Oliver
(Continued)

FOREIGN PATENT DOCUMENTS

CN   1175217 A   3/1998
CN   1178475 A   4/1998
(Continued)

OTHER PUBLICATIONS

Extended European Search Report and Written Opinion dated Oct. 17, 2022, for Application No. 20873352.7, 15 pages.
(Continued)

*Primary Examiner* — Bradley J Osinski
(74) *Attorney, Agent, or Firm* — FROST BROWN TODD LLP

(57) ABSTRACT

The present disclosure relates to an injection head of a needleless syringe, needleless syringe body, and needleless syringe. The injection head includes a medicine barrel and a piston rod. The medicine barrel opens at a rear end and has an injection micropore at a front end. A piston of a piston rod is movable within a chamber in an front-rear direction, the piston and a sidewall and a front wall of the medicine barrel jointly define a medicine liquid receiving chamber. The piston rod is provided therein with a medicine liquid channel. The injection head and the vial can be mounted together on the needleless syringe body, the medicine liquid can flow via the medicine liquid channel into the medicine liquid chamber, and the piston rod can eject medicine liquid within the medicine liquid receiving chamber outside via the injection micropore. According to the solution of the present
(Continued)

disclosure, a vial, such as a cartridge vial and the like, can be received within a needleless syringe body, and medicine suctioning and injection can be completed efficiently and effortlessly during each use, where there is no need for removing the vial or separating the medicine barrel from the vial.

24 Claims, 29 Drawing Sheets

(56) References Cited

U.S. PATENT DOCUMENTS

| | | | |
|---|---|---|---|
| 5,695,465 | A | 12/1997 | Zhu |
| 5,846,233 | A | 12/1998 | Lilley et al. |
| 2004/0015126 | A1 | 1/2004 | Zierenberg et al. |
| 2004/0133163 | A1 | 7/2004 | Schiffmann |
| 2005/0209553 | A1 | 9/2005 | Landau |
| 2009/0105685 | A1 | 4/2009 | Hansen et al. |
| 2012/0302947 | A1* | 11/2012 | Canton ................ A61M 5/30 604/68 |

FOREIGN PATENT DOCUMENTS

| | | |
|---|---|---|
| CN | 1407906 A | 4/2003 |
| CN | 1921931 A | 2/2007 |
| CN | 200966816 Y | 10/2007 |
| CN | 101437560 A | 5/2009 |
| CN | 201524322 U | 7/2010 |
| CN | 203263947 U | 11/2013 |
| CN | 103550848 A | 2/2014 |
| CN | 203447586 U | 2/2014 |
| CN | 106917887 A | 7/2017 |
| CN | 109432554 A | 3/2019 |
| CN | 110279914 A | 9/2019 |
| CN | 111558112 A | 8/2020 |
| CN | 111558113 A | 8/2020 |
| JP | 2007-512054 A | 5/2007 |
| WO | WO 2001/089613 A1 | 11/2001 |
| WO | WO 2016/181377 A1 | 11/2016 |
| WO | WO 2021/206553 A1 | 10/2021 |

OTHER PUBLICATIONS

Japanese Notification of Reasons for Refusal dated Oct. 28, 2022, for Application No. 2021-521357, 7 pages.
Partial Supplementary European Search Report and Written Opinion dated Jul. 13, 2022, for Application No. 20873352.7, 15 pages.
Chinese Office Action dated Mar. 30, 2021, for Application No. 202010366995.9, 11 pages.
Chinese Office Action dated Mar. 30, 2021, for Application No. 202010367033.5, 12 pages.
International Search Report and Written Opinion dated Feb. 10, 2021 for International Application No. PCT/CN2020/127824, 14 pages.

* cited by examiner

INJECTION HEAD OF NEEDLELESS SYRINGE, NEEDLELESS SYRINGE BODY AND NEEDLELESS SYRINGE

FIELD

The present disclosure relates to a medical instrument for injecting liquid medicine, and more particularly, to an injection head of a needleless syringe, needleless syringe and needleless syringe assembly.

BACKGROUND

A needleless syringe is a medical instrument which injects liquid medicine subcutaneously into a patient via a micropore at its end, without use of a needle, to relieve the pain caused by sting. The needleless syringe typically includes a medicine barrel for receiving liquid medicine, and a plunger.

When a needleless syringe is used, following steps are often involved: first mounting the medicine barrel onto the needleless syringe, then suctioning a medicine from the vial via the needle at the front end of the medicine barrel, and performing injection after the medicine barrel is separated from the vial. It is seen therefrom that the medicine suctioning operation is cumbersome.

In connection with this problem, a method has been provided in which the medicine barrel and the vial are combined as one for single use. However, such method incurs high costs, and the material for the combination of the medicine barrel and the vial cannot meet safety requirements of long-term drug contact.

Therefore, there arises a need for an injection head of a needleless syringe, needleless syringe body, and needleless injection assembly, to at least partly solve the above-mentioned problem.

SUMMARY

In order to cure the above deficiency, the present disclosure provides an injection head of a needleless syringe, needleless syringe body, and needleless syringe. According to the solution of the present disclosure, a vial, such as a cartridge vial and the like, can be received within a needleless syringe body, and medicine suctioning and injection can be completed efficiently and effortlessly during each use, where there is no need for removing the vial or separating the medicine barrel from the vial. Furthermore, as the vial is received within the needleless syringe body, issues such as vial loss, contamination, and the like can be prevented.

According to an aspect of the present disclosure, there is provided an injection head of a needleless syringe body, which is configured to be used with a vial, the injection head comprising:
- a medicine barrel provided therein with a chamber which opens at its rear end, a front end of the medicine barrel being formed with an injection micropore communicating the chamber with the outside;
- a piston rod comprising:
- a piston disposed within the chamber and configured to move within the chamber in an front-rear direction, the piston configured to define, together with a sidewall and a front wall of the medicine barrel, a medicine liquid receiving chamber;
- a rod portion fixedly connected at a rear end of the piston;

wherein, in use, a rear end of the rod portion of the injection head is configured to be inserted and extend into the vial, and the piston rod is provided therein with a medicine liquid channel communicating the medicine liquid receiving chamber with the vial, wherein the injection head and the vial can be mounted together to a body of the needleless syringe, and the piston rod is configured to move rearwards relative to the medicine barrel to suck medicine liquid into the medicine liquid receiving chamber via the medicine liquid channel, and move forwards relative to the medicine barrel to eject medicine liquid within the medicine liquid receiving chamber outside via the injection micropore.

In an embodiment, the medicine liquid channel extends along an axis direction of the piston rod, and the piston rod at a front end is provided with a check valve only allowing the medicine liquid from the vial into the medicine liquid receiving chamber.

In an embodiment, the check valve comprises a valve core embedded within the piston and configured to move relative to the piston in the front-rear within a small range, and the medicine liquid from the vial flows through a gap between the valve core and the piston into the medicine liquid receiving chamber.

In an embodiment, the valve core is of a spherical structure; or a front portion of the valve core is of a conical structure while a rear portion is of a cylindrical structure connected to a bottom of the conical structure, a diameter of the bottom of the conical structure being greater than a diameter of the cylindrical structure.

In an embodiment, the piston is provided thereon with a piston inner channel extending parallel to the axis direction, an interval is provided between the piston inner channel and the piston rod in a radial direction about the axis, and the medicine fluid from the vial flows through the piston inner channel into the medicine fluid receiving chamber.

In an embodiment, a rear end of the rod portion is of a needle-like structure for puncturing a sealing film of the vial.

In an embodiment, the injection head further comprises a cap for closing the micropore removably disposed at the front end of the medicine barrel.

In an embodiment, the piston rod is configured to be fixed relative to the vial in use; or
the piston rod is configured to move rearwards relative to the vial when moving rearwards relative to the medicine barrel, to compress a medicine storage space within the vial.

In another aspect of the present disclosure, there is provided a needleless syringe body for use with the injection head according to any item of the above-mentioned solution and a vial, characterized in that the needleless syringe body comprises:
- a base comprising a forward opening;
- an outer housing comprising a rearward opening and mounted at a front end of the base to form a receiving space between the base and the outer housing, the outer housing being provided with a front opening for fixedly mounting a medicine barrel;
- an inner push rod disposed within the receiving space and having a forward opening, the vial is fixedly received within the inner push rod, the piston rod fixed at the forward opening,
- wherein the outer housing can move in an front-rear direction relative to the inner push rod to drive the medicine barrel to move in an front-rear direction relative to the vial and the piston rod, so as to implement medicine suctioning and injection.

In an embodiment, the needleless syringe body further comprises a locking mechanism connected between the base and the inner push rod, and the locking mechanism is configured to lock the inner push rod relative to the base in a medicine suctioning process, and unlock the inner push after medicine suction to cause the inner push rod to move forwards relative to the outer housing.

In an embodiment, the inner push rod at a rear end is provided with a rear end flange protruding radially outwards, and the locking mechanism comprises:
a limiting member configured to abut against a front end face of the rear end flange in a locked state to limit forward movement of the inner push rod;
a button mounted on a rear end wall of the base and protruding rearwards relative to the base,
wherein the button is configured to be pushed to move forward relative to the base and apply directly or indirectly a thrust to a rear end face of the inner push rod, and the rear end flange of the inner push rod can pass over the limiting member as an effect of the thrust, causing the locking mechanism to unlock the inner push rod.

In an embodiment, the locking mechanism further comprises:
a spring receiving member disposed between a rear end face of the inner push rod and a rear end wall of the button and having a spring receiving chamber opening rearwards;
a button spring disposed in the spring receiving chamber and configured to contact at its rear end with the button;
wherein the button can be pushed to indirectly apply a thrust to the inner push rod via the button spring and the spring receiving member.

In an embodiment, the button has a rear end wall, and a sidewall extending forwards from the rear end wall and surrounding the axis, the sidewall at a front end is provided with a protrusion portion protruding towards an axis of the needleless syringe body, and the limiting member is configured to move relative to the button in a radial direction relative to the axis,
wherein, in a locked state, the protrusion portion abuts against a radial outside of the limiting member to limit radial outward movement thereof, the protrusion portion moves forwards relative to the limiting member when the button is pushed, to release radial restrictions thereon, and at this time, the limiting member can move radially outwards to disengage from the front end face of the rear end flange, thereby unlocking the inner push rod.

In an embodiment, the limiting member is a sphere, and a rear end face of the protrusion portion and a front end face of the rear end flange are slopes, such that the limiting member can be in rolling contact with the slopes during unlocking.

In an embodiment, the locking mechanism is an electromagnet.

In an embodiment, the needleless syringe body further comprises a resilient actuation mechanism disposed between the base and the inner push rod, which is configured to be operated before injection for energy accumulation, and to be released after energy accumulation to actuate the inner push rod forwards via a resilient force to complete injection.

In an embodiment, the inner push rod at an inner end is provided with a front end flange protruding radially outwards, and the resilient actuation mechanism comprises an actuation spring disposed between the front end flange and the base.

In an embodiment, the actuation spring is sleeved outside the inner push rod.

In an embodiment, a spring shaft 37 is fixedly connected on a front end flange of the inner push rod, which is parallel to an axis of the inner push rod and onto which the actuation spring is sleeved.

In an embodiment, a plurality of the spring shafts are provided, each being sleeved thereon with the actuation spring, the spring shafts being arranged around the inner push rod.

In an embodiment, the inner push rod in the middle is provided with a middle flange disposed along its peripheral direction, and the spring actuation mechanism comprises an actuation spring between the middle flange and the base.

In an embodiment, the base comprises a rear end portion and a base sidewall, the base sidewall at an inner surface is provided with internal threads, the outer housing at a rear outer surface is provided with external threads corresponding to the internal threads, and cooperation of the internal threads and the external threads enables the outer housing to move rearwards relative to the base, thereby stably compressing the actuation spring.

In an embodiment, respective portions of the outer housing and the inner push rod facing the vial in a radial direction are configured to be at least partly transparent or hollow, making a volume of medicine liquid within the vial visible.

According to a further aspect of the present disclosure, there is provided a needleless syringe, comprising the needleless syringe body according to any item of the above-mentioned solution and an injection head for use with the needleless syringe body.

In an embodiment, an outer housing of the needleless syringe body at a front opening is provided with internal threads facing an axis of the needleless syringe, a medicine barrel of the injection head is provided with external threads, and with cooperation of the internal threads and the external threads, the medicine barrel can be removably mounted on the needleless syringe body.

According to a still further aspect, there is provided a needleless syringe body for use with an injection head and a vial, the vial comprising a vial body having a vial receiving chamber, and a cork slidable within the vial receiving chamber in an front-rear direction relative to the vial body, characterized in that the needleless syringe body comprises:
a base having a forward opening;
an outer housing having a rearward opening and mounted at a front end of the base to form a receiving space between the base and the outer housing, the outer housing provided with a front opening for fixedly mounting a medicine barrel;
an inner push rod system comprising an inner push rod disposed within the receiving space and having a forward opening, the vial is fixedly received within the inner push rod, the piston rod is fixed at the forward opening;
a medicine supply push rod mounted at a rear end of the inner push rod, the medicine supply push rod at a front end being in contact with the cork of the vial; and
transmission means, wherein a part of the transmission means is connected to the medicine supply push rod while the other part thereof is directly or indirectly connected to the base or the outer housing,
wherein the outer housing can move in an front-rear direction relative to the inner push rod, to drive the medicine barrel to move in the front-rear direction relative to the vial and the piston rod, to implement medicine suctioning and injection, and wherein, in a medicine suctioning process, the base or the outer housing drives, via the transmission means, the medicine supply push rod to move the cork of the vial forwards relative to the vial body, so as to compress a space within the vial.

In an embodiment, the needleless syringe body further comprises a locking mechanism connected between the base and the inner push rod system, which is configured to lock the inner push rod system in a medicine suctioning process to lock the inner push rod system in an front-rear direction relative to the base, and to unlock the inner push rod system after medicine suctioning to move forwards relative to the outer housing.

In an embodiment, the base and the outer housing are engaged and being rotatable relative to each other, such that, through relative rotation between the outer housing and the base, relative movement of the two can be achieved in an axis direction of the needleless syringe body.

In an embodiment, the inner push rod system further comprises a transmission rod which is connected at a front end to the transmission means and engaged at a rear end with the locking mechanism, and the transmission rod is fixed relative to the base in a rotational direction relative to the base when locked by the locking mechanism.

In an embodiment, the transmission means comprises transmission means for rotational movement which is configured to transmit specified rotational movement of the transmission rod to the medicine supply push rod to drive the medicine supply push rod to rotate; and the needleless syringe body is provided therein with a movement conversion mechanism, and a part of the movement conversion mechanism is engaged with the medicine supply push rod while the other part of the movement conversion mechanism is directly or indirectly engaged with the inner push rod to convert rotational movement of the medicine supply push rod along with the transmission rod into linear movement of the inner push rod.

In an embodiment, in the medicine suctioning process, the outer housing rotates relative to the base to move forwards relative to the same; and the transmission means for rotational movement comprises one-way transmission means for rotational movement which is configured to transmit the rotational movement of the transmission rod to the medicine supply push rod when the outer housing rotates relative to the base to move forwards relative to the base, and not to transmit the rotational movement of the transmission rod to the medicine supply push rod when the outer housing rotates relative to the base to move rearwards relative to the same.

In an embodiment, the one-way transmission means for rotational movement comprises a one-way bearing, which is fixedly connected at an outer ring to the transmission rod, and fixedly connected at an inner ring to the medicine supply push rod in a rotational direction about the axis of the needleless syringe body.

In an embodiment, the movement conversion mechanism comprises a nut member received in a receiving space of the inner push rod and fixedly connected to the inner push rod, and the medicine supply push rod is engaged with the nut member in thread fit.

In an embodiment, the nut member comprises at least two nut members separated from each other, which are arranged around the medicine supply push rod and can move towards or away from the axis of the needleless syringe body in a radial direction of the needleless syringe body, so as to engage with or disengage from the medicine supply push rod.

In an embodiment, the at least two nut members are configured to move radially in a direction away from the axis and thus disengage from the medicine supply push rod, when the medicine supply push rod applies a force in an axial direction of the needleless syringe body to the nut members and the force reaches a predetermined threshold.

In an embodiment, a resilient member is mounted between circumferential outer surfaces of the nut members and a circumferential inner surface of the inner push rod, which is compressed when the two nut members disengage from the medicine supply push rod.

In an embodiment, the needleless syringe body further comprises a nut limiting member at a front end of each of the nut members, wherein a surface of the nut member contacting with the nut limiting member is a force bearing slope, a rear end of the force bearing slope is radially farther away from the axis of the needleless syringe than a front end thereof, and the nut limiting member is configured to urge the force bearing slope rearwards to press the nut member into engagement with the medicine supply push rod, and to cause, when stopping applying the force to the nut member, the nut member to move radially away from the other and thus disengage from the medicine supply push rod.

In an embodiment, the front end of the nut limiting member can be in direct contact with a rear end of the vial body, to press the nut member continuously as an effect of a rearward force of the vial body when the vial is mounted within the inner push rod, and the nut limiting member stops applying the force to the nut limiting member after the vial is removed from the inner push rod.

In an embodiment, the nut limiting member is a wedge which has a force applying slope contacting with the force bearing slope.

In an embodiment, the nut limiting member is of a spherical structure, and a sphere movement slot is provided at a front end of a radial outer edge of the nut member, within which the nut limiting member is limited, making it impossible to escape therefrom.

In an embodiment, the nut limiting member is of an annular structure coaxial with the needleless syringe body, and a section of the annular structure after cut by a plane where its axis is located is circular.

In an embodiment, the inner push rod system at a rear end is provided with a rear end flange protruding radially outwards, and the locking mechanism comprises:
  a limiting member configured to abut in a locked state against a front end face of the rear end flange to limit forward movement of the inner push rod system;
  a button mounted at a rear end wall of the base and protruding rearwards from the base,
  wherein the button is configured to be pushed to move forwards relative to the base and to directly or indirectly apply a thrust to a rear end face of the inner push rod system, and the rear end flange of the inner push rod system can pass over the limiting member as an effect of the thrust, thereby causing the locking mechanism to unlock the inner push rod system.

In an embodiment, the locking mechanism further comprises:

a spring receiving member disposed between a rear end face of the inner push rod system and a rear end wall of the button and having a spring receiving chamber opening rearwards;

a button spring disposed within the spring receiving chamber and configured at its rear end to contact with button, wherein the button can be pushed to indirectly apply a thrust to the inner push rod system via the button spring and the spring receiving member.

In an embodiment, the button has a rear end wall and a sidewall extending forwards from the rear end wall and around the axis, the side wall at a front end is provided with a protrusion portion protruding towards an axis of the needleless syringe body, and the limiting member is configured to move relative to the button in a radial direction relative to the axis, wherein, in a locked state, the protrusion portion abuts against a radial outside of the limiting member to limit radial outward movement thereof, the protrusion portion moves forwards relative to the limiting member when the button is pushed, to release radial restrictions thereon, and at this time, the limiting member can move radially outwards to disengage from a front end face of the rear end flange, thereby unlocking the inner push rod system.

In an embodiment, the limiting member is a sphere, and a rear end face of the protrusion portion and a front end face of the rear end flange are both slopes such that the limiting member can be in rolling contact with the slopes in the unlocking process.

In an embodiment, the locking mechanism is an electromagnet.

In an embodiment, the needleless syringe body further comprises a resilient actuation mechanism disposed between the base and the inner push rod system, which is configured to be operated for energy accumulation prior to injection, and to be released after energy accumulation to actuate the inner push rod system forwards, so as to complete injection.

In an embodiment, the inner push rod at a front end is provided with a front end flange protruding radially outwards, and the resilient actuation mechanism comprises an actuation spring disposed between the front end flange and the base.

In an embodiment, the actuation spring is sleeved outside the inner push rod.

In an embodiment, a spring shaft is fixedly connected at the front end flange of the inner push rod, which is parallel to an axis of the inner push rod and onto which the actuation spring is sleeved.

In an embodiment, a plurality of the spring shafts are provided, each being sleeved thereon with the actuation spring, the spring shafts being arranged around the inner push rod.

In an embodiment, the inner push rod in the middle is provided with a middle flange disposed along its peripheral direction, and the spring actuation mechanism comprises an actuation spring between the middle flange and the base.

In an embodiment, the base comprises a rear end portion and a base sidewall, the base sidewall at an inner surface is provided with internal threads, the outer housing at a rear outer surface is provided with external threads corresponding to the internal threads, and cooperation of the internal threads and the external threads enables the outer housing to move rearwards relative to the base, thereby stably compressing the actuation spring.

In an embodiment, respective portions of the outer housing and the inner push rod facing the vial in a radial direction are configured to be at least partly transparent or hollow, making a volume of medicine liquid within the vial visible.

In an embodiment, the inner push rod at an outer periphery is provided with an inner push rod flange protruding radially outwards, a circumferential outer surface of the inner push rod flange is in contact with a circumferential inner surface of the outer housing, and the circumferential outer surface of the inner push rod flange and the circumferential inner surface of the outer housing are provided with a movement limiting feature which is configured to limit rotation of the inner push rod relative to the outer housing while permitting the inner push rod to move in an front-rear direction relative to the outer housing.

In an embodiment, the movement limiting feature comprises a keyway or guide rod formed on the circumferential outer surface of the inner push rod flange and the circumferential inner surface of the inner housing and extending along an axis direction of the needleless syringe body.

According to a still another aspect of the present disclosure, there is provided a needleless syringe, comprising the needleless syringe body according to any item of the solution and an injection head for use with the needleless syringe body.

In an embodiment, the injection head can be used with a vial, the injection head comprising:

a medicine barrel provided therein with a chamber which opens at its rear end, a front end of the medicine barrel being formed with an injection micropore communicating the chamber with the outside;

a piston rod comprising:

a piston disposed within the chamber and configured to move within the chamber in an front-rear direction, the piston configured to define, together with a sidewall and a front wall of the medicine barrel, a medicine liquid receiving chamber;

a rod portion fixedly connected at a rear end of the piston;

wherein, in use, a rear end of the rod portion of the injection head is configured to be inserted and extend into the vial, and the piston rod is provided therein with a medicine liquid channel communicating the medicine liquid receiving chamber with the vial, wherein the injection head and the vial can be mounted together on a body of the needleless syringe, and the piston rod is configured to move rearwards relative to the medicine barrel to suck medicine liquid into the medicine liquid receiving chamber via the medicine liquid channel, and move forwards relative to the medicine barrel to eject medicine liquid within the medicine liquid receiving chamber outside via the injection micropore.

In an embodiment, the medicine liquid channel extends along an axis direction of the piston rod, and the piston rod at a front end is provided with a check valve only allowing the medicine liquid from the vial into the medicine liquid receiving chamber.

In an embodiment, the check valve comprises a valve core embedded within the piston and configured to move relative to the piston in the front-rear within a small range, and the medicine liquid from the vial flows through a gap between the valve core and the piston into the medicine liquid receiving chamber.

In an embodiment, the valve core is of a spherical structure; or a front portion of the valve core is of a conical structure while a rear portion is of a cylindrical structure connected to a bottom of the conical structure, a diameter of the bottom of the conical structure being greater than a diameter of the cylindrical structure.

In an embodiment, the piston is provided with thereon with a piston inner channel extending parallel to the axis direction, an interval is provided between the piston inner channel and the piston rod in a radial direction about the axis, and the medicine fluid from the vial flows through the piston inner channel into the medicine fluid receiving chamber.

In an embodiment, a rear end of the rod portion is of a needle-like structure for puncturing a sealing film of the vial.

In an embodiment, the injection head further comprises a cap for closing the micropore removably disposed at the front end of the medicine barrel.

In an embodiment, internal threads facing an axis of the needleless syringe are disposed at a front opening of an outer housing of the needleless syringe body, external threads are provided on the medicine barrel of the injection head, and cooperation of the internal threads and the external threads enables removable mounting of the medicine barrel on the needleless syringe body.

According to the present disclosure, a vial, such as a cartridge vial and the like, can be received within a needleless syringe body, and medicine suctioning and injection can be completed efficiently and effortlessly during each use, where there is no need for removing the vial or separating the medicine barrel from the vial. Furthermore, as the vial is received within the needleless syringe body, issues such as vial loss, contamination, and the like can be prevented.

BRIEF DESCRIPTION OF THE DRAWINGS

For the sake of better understanding on the above and other objectives, features, advantages, and functions of the present disclosure, preferred embodiments are provided with reference to the drawings. The same or similar reference symbols refer to the same or similar components throughout the drawings. It would be appreciated by those skilled in the art that the drawings are merely provided to illustrate preferred embodiments of the present disclosure, without suggesting any limitation to the protection scope of the present disclosure, and respective components therein are not necessarily drawn to scale.

DETAILED DESCRIPTION OF EMBODIMENTS

Reference now will be made to the drawings to describe a needleless syringe, needleless syringe body, and injection head of the needleless syringe. What will be described herein are only preferred embodiments according to the present disclosure. On the basis of the preferred embodiments, those skilled in the art would envision other embodiments which also fall into the scope of the present disclosure.

The present disclosure provides an injection head of a needleless syringe, a needleless syringe body and the needleless syringe. FIGS. 1-34B illustrate some preferred embodiments according to the present disclosure.

It is worth noting that the "axial direction" here is to be read as a direction of an axis X of the needleless syringe; in the axis direction, a direction facing a patient during use of the needleless syringe is referred to as "front side", while the opposite direction is referred to as "rear side". The "radial direction" here is to be read as radial direction about the axis direction, which is denoted by X' in FIG. 15.

Figure 1:
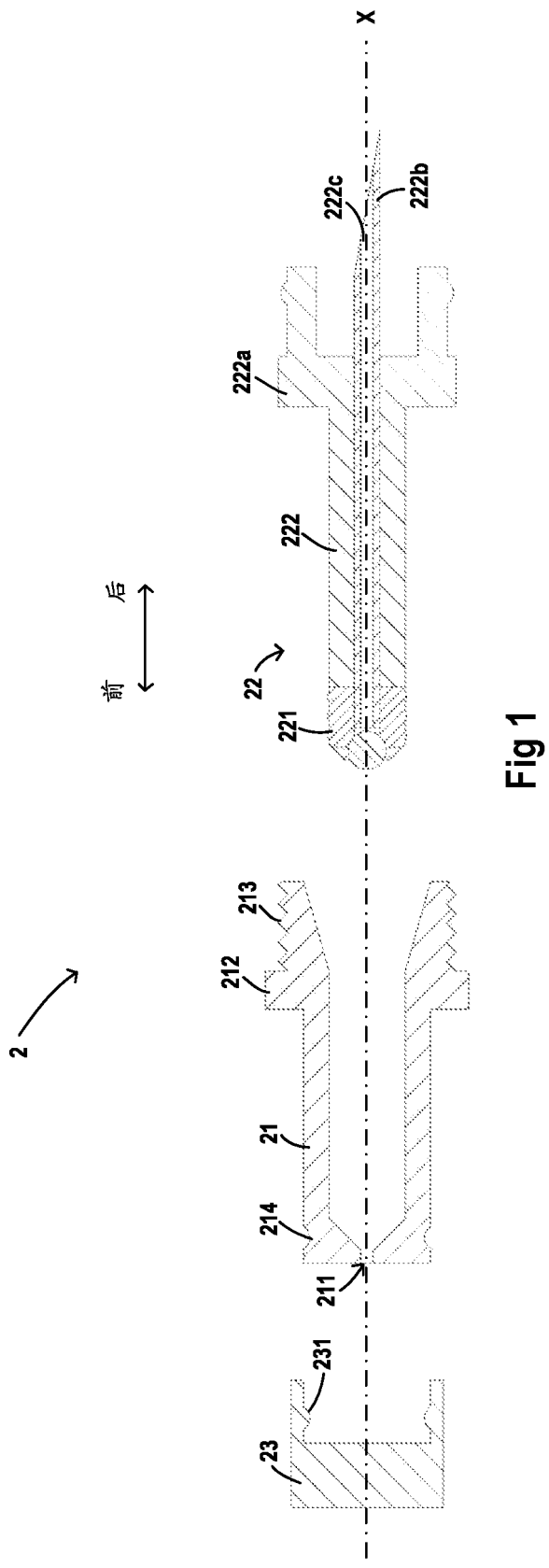
FIG. 1 is a section view of an injection head of a needleless syringe according to a preferred embodiment of the present disclosure in a explosive state.
Figure 2:
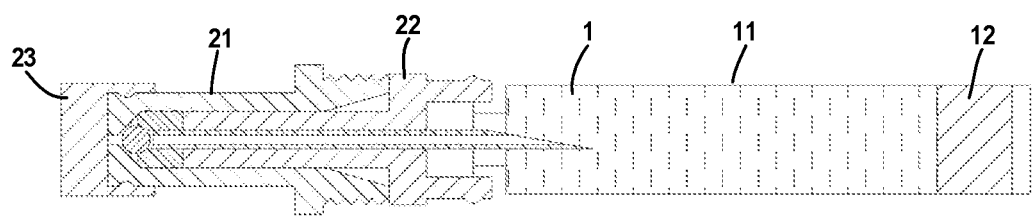
FIG. 2 is a section view of the injection head in FIG. 1 in a state connected to a vial.
Figure 3:
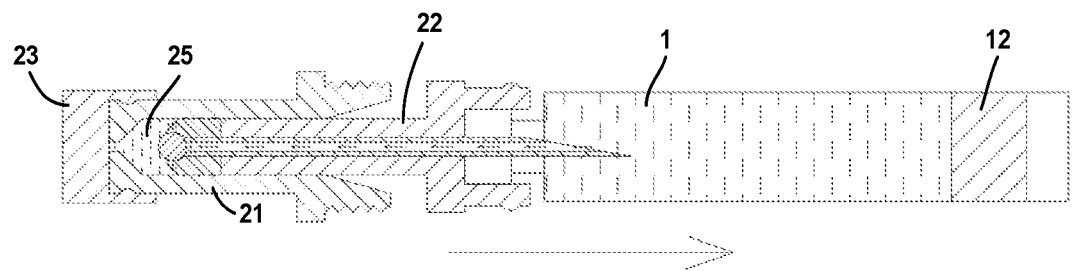
FIG. 3 is a section view of the injection head in FIG. 2 during a medicine suctioning process.
Figure 4:
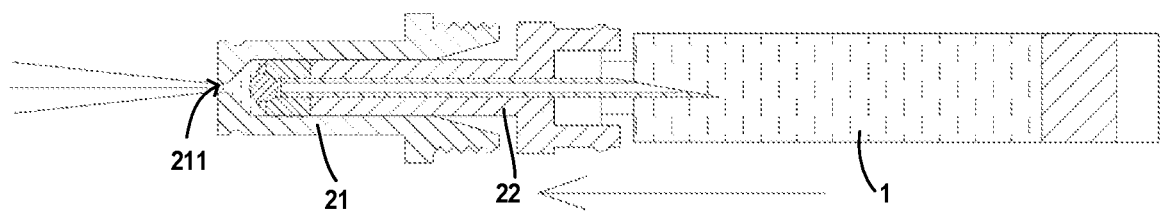
FIG. 4 is a section view of the injection head in FIG. 2 during an injection process.

FIG. 1 is a schematic diagram of an injection head 2 of a needleless syringe according to a preferred embodiment in a explosive state. The injection head 2 is used with a vial 1 which may be a cartridge vial in line with the national standards, for example. FIGS. 2-4 are schematic diagrams illustrating a connection between the injection head 2 and the vial 1, in which the injection head 2 and the vial 1, if connected correctly, can be mounted jointly on the needleless syringe body 3 (see FIG. 11).

As can be seen from FIGS. 1-4, the injection head 2 is substantially a rotational symmetric structure about an axis X, and specifically includes a medicine barrel 21 and a piston rod 22. The medicine barrel 21 is provided therein with a chamber that opens at the rear end. An injection micropore 211 communicating the chamber with the outside is formed at the front end of the medicine barrel 21. The piston rod 22 includes a piston 221 and a rod portion 222, where the piston 221 is disposed within the chamber and movable within the chamber in an front-rear direction, the piston 221 and the sidewall and front wall of the medicine barrel 21 can jointly define a medicine liquid receiving chamber 215, and the rod portion 222 is fixedly connected at the rear end of the piston 221 and extends into the vial 1. Moreover, the piston rod 22 is provided therein with a liquid medicine channel 222c for communicating the medicine liquid receiving chamber 215 with the vial 1. The liquid medicine channel 222c preferably extends along the axis X.

Preferably, the rear end of the rod portion 222 is of a needle-like structure 222b for puncturing a sealing film at the front end of the vial 1. Similarly preferably, the injection head 2 may further include a cap 23 removably disposed at the front end of the vial 221 for closing the injection micropore 211. The cap 23 may be provided thereon with a cap protrusion 231, the medicine barrel may be provided thereon with a medicine barrel recess 214, and the cap protrusion 231 and the medicine barrel recess 214 can engage with each other to enable convenient mounting of the cap 23 on the medicine barrel 21. In other embodiments not shown, a cap 23 may not be provided additionally, and the medicine barrel 21 is configured to cause the injection micropore 211 to be self-opened and self-closed.

Referring to FIG. 3, when the cap 23 is mounted at the front end of the medicine barrel 21, the piston rod 22 moves rearwards relative to the medicine barrel 21. At this time, negative pressure is formed within the medicine liquid receiving chamber 215 to suction the medicine liquid within the vial 1 via the medicine liquid channel 222c into the medicine liquid receiving chamber 215. Preferably, a rear end of a medicine storage space of the vial 1 may be closed by a movable cork 12 which is configured to move freely relative to the vial body 11 under the gas pressure. In other words, during the medicine suctioning process, the cork 12 can move forwards relative to the vial body 11 to ensure that the pressure within the medicine storage space is not reduced to keep the medicine suctioning rate at a stable level throughout the whole process. Referring to FIG. 4, after completion of medicine suction, the cap 23 may be removed, and the piston rod 22 is controlled to move forwards relative to the medicine barrel 21, so as to eject the medicine liquid within the medicine liquid receiving chamber 215 via the injection micropore 211.

In order to prevent the medicine fluid from flowing back from the medicine fluid receiving chamber 215 into the vial 1 and thus cause contamination, the piston rod 22 at the front end may be provided with a check valve which is configured to only allow the medicine liquid to flow from the vial 1 into the medicine liquid receiving chamber 215. FIGS. 5 to 10 illustrate three embodiments of the check valve.

Two types of check valves as shown in FIGS. 5-8 include a valve core embedded in the piston 221, and the valve core is movable in a small range relative to the piston 221 in an anterior-posterior direction. The valve core is formed in a rotatable symmetric structure relative to the axis. The medicine liquid from the vial 1 should flow through a gap between the valve core and the piston 221 into the medicine liquid receiving chamber 215. In other embodiments not shown, the valve core may be of an asymmetric structure. Specifically, in this embodiment, due to the negative pressure in the medicine suctioning process, the piston 221 is deformed, and the valve core is moved slightly forwards relative to the piston 221 under the suctioning force, such that a path can be formed between the valve core and the piston 221. Upon completion of the medicine suctioning, movement of the piston rod 22 is stopped. At this time, the medicine liquid is supplied via the path into the medicine liquid receiving chamber, and the negative pressure disappears. In particular, after the cap 23 is removed from the medicine barrel 21, the pressure within the medicine liquid receiving chamber is identical to the external pressure due to the micropore 211 at the front end of the medicine barrel 21. By this time, the valve core is forced back to the original site to prevent backflow of the medicine liquid.

Figure 5:
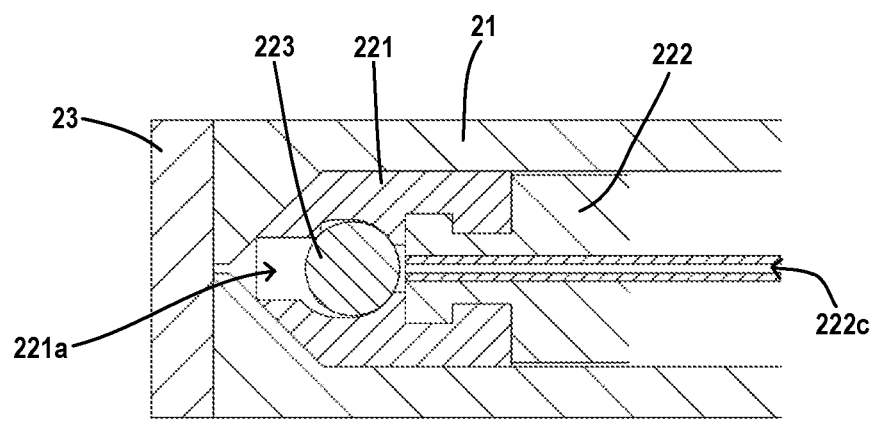
FIGS. 5 and 6 are section views of a front end of the injection head in FIG. 2 at a prepared state and a medicine suctioning state, respectively.
Figure 6:
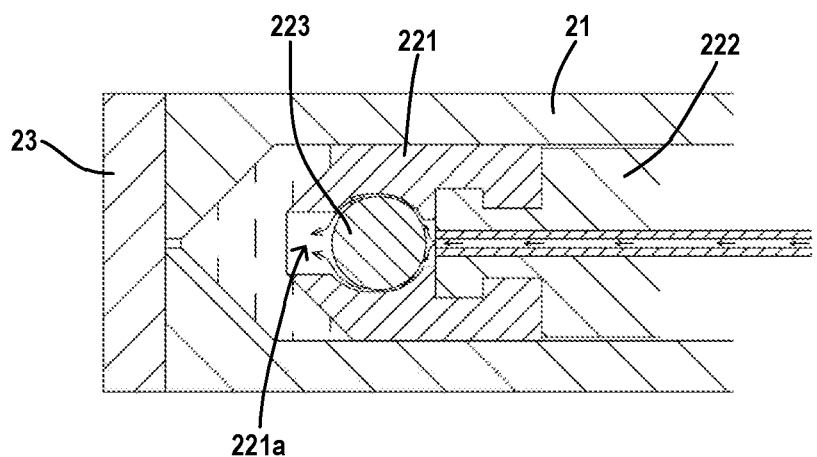

Specifically, the check valve according to an embodiment as shown in FIGS. 5 and 6 is a ball valve, where the valve core 223 is spherical, and the piston 221 is provided with a receiving structure adapted to the outer contour of the sphere. FIG. 5 is schematic diagram when no medicine liquid flows through the valve core 223, and FIG. 6 is a schematic diagram when a medicine liquid flows through the valve core 223. As shown in FIG. 6, the medicine liquid reaches the valve core 223 via the medicine liquid channel 222c and then flows through the gap between the valve core 223 and the piston 221 (i.e., bypassing the valve core 223) into the medicine liquid receiving chamber 215.

Figure 7:
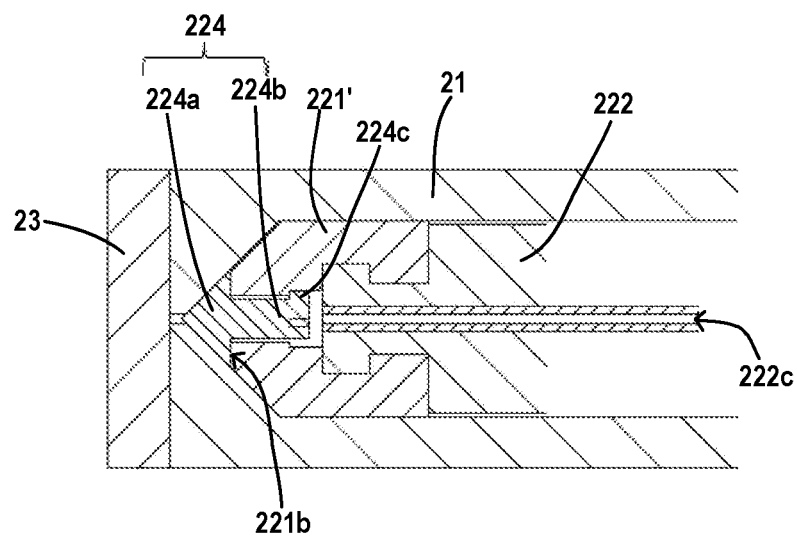
FIGS. 7-8 are section views of an alternative solution of the in FIGS. 5-6.
Figure 8:
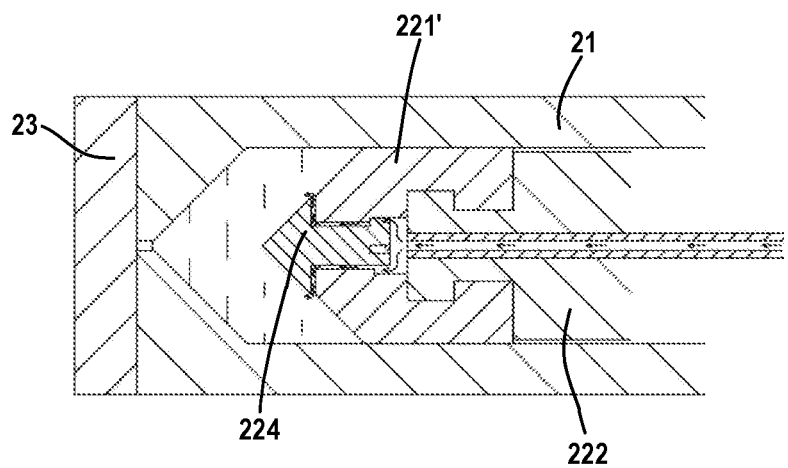

A valve core 224 of a check valve according to a further embodiment as shown in FIGS. 7 and 8 includes two portions, namely a front portion which is a conical structure 224a and a rear portion which is a cylindrical structure 224b, where the cylindrical structure 224b is connected to the bottom of the conical structure 224a, and the diameter of the bottom of the conical structure 224a is greater than the diameter of the cylindrical structure 224b. Preferably, the front end face 221b of the piston 221' matches the rear end face of the conical structure 224a, and when the valve core 224 is mounted on the piston 221', the front end of the whole structure of the valve core 224 and the piston 221' happens to form a conical structure. The valve core 224 is formed of a resilient material. During the medicine suctioning process, due to the negative pressure within the medicine liquid receiving chamber (there additionally exists the impact of the medicine liquid), the front end of the conical structure 224 is subjected to a forward suction force. On the other hand, the cylindrical portion 224b at the rear end is provided with a small protrusion 224c engaging with the piston 221', and since the front end of the valve core 224 is subjected to a forward suction force while the rear end is fixed relative to the piston 221', the valve core 224 is slightly deformed, causing the conical portion 224a of the valve core 224 to move slightly forwards relative to the piston 221', such that a gap is formed between the conical portion 224a of the valve core 224 and the piston 221' through which the medicine liquid can flow into the medicine liquid receiving chamber 215.

Figure 9:
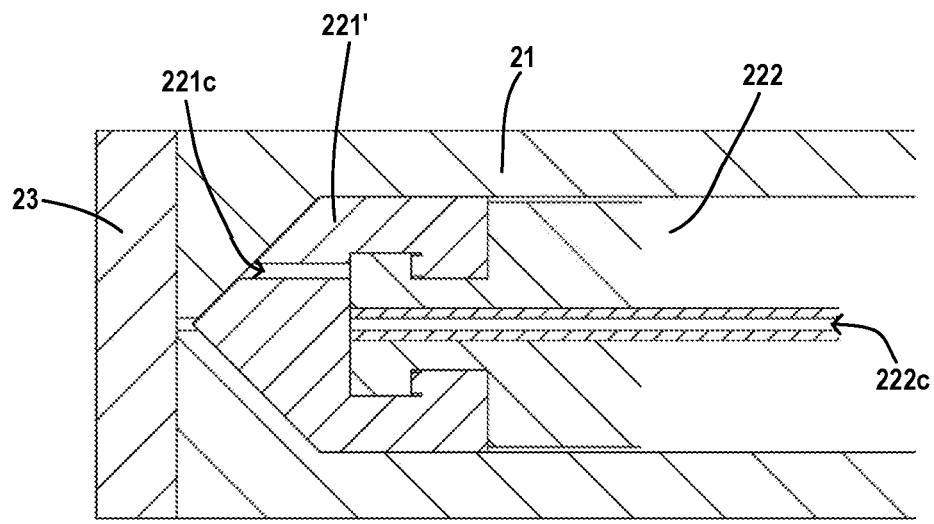
FIGS. 9-10 are section views of a further alternative solution of the in FIGS. 5-6.
Figure 10:
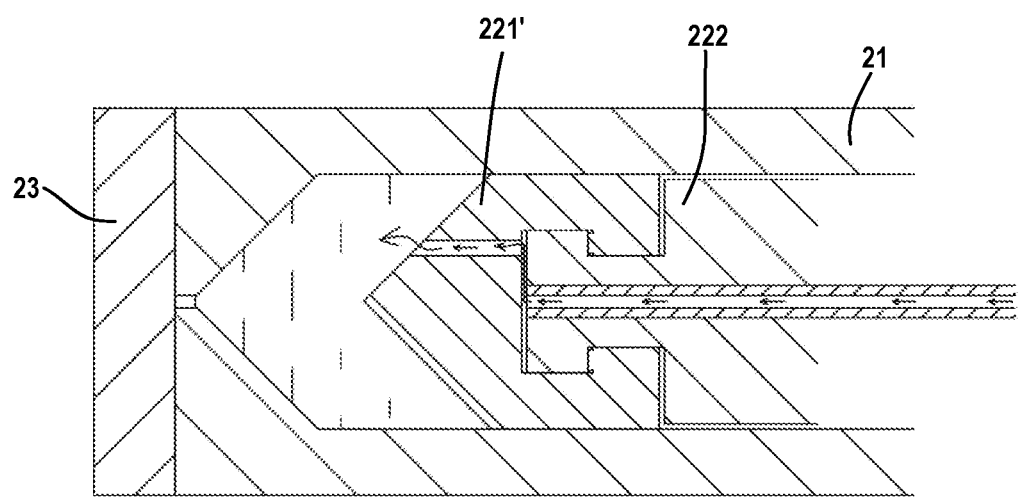

FIGS. 9 and 10 illustrate a check valve structure according to a further embodiment. The check valve in FIGS. 9 and 10 is not provided with a valve core, but the piston 211" is provided therein with a piston inner channel 221c which may be parallel to the axial direction, or angled relative to the axial direction. The piston inner channel 221c and the piston rod 22 are spaced apart in the radial direction about the axis. The medicine liquid from the vial 1 flows sequentially through the medicine liquid channel 222c within the rod portion 222 and the piston inner channel 221c within the piston 221" into the medicine liquid receiving chamber 215.

In the embodiment as shown, the piston rod 22 is fixed relative to the vial 1 during medicine suctioning and injection operations, and the medicine liquid is introduced from the vial 1 into the medicine liquid receiving chamber 214 in the medicine suctioning process, only as an effect of a difference between pressures within the medicine liquid receiving chamber 215 and the vial 1. However, in other embodiments not shown, the piston rod 22 at the rear end may be provided with a piston movable within the vial. During the medicine suctioning process, the piston rod 22 moves rearwards relative to both the medicine barrel 21 and the vial 1, thereby compressing the space within the vial by a piston within the vial. Such operation can further increase the medicine suctioning rate.

Figure 11:
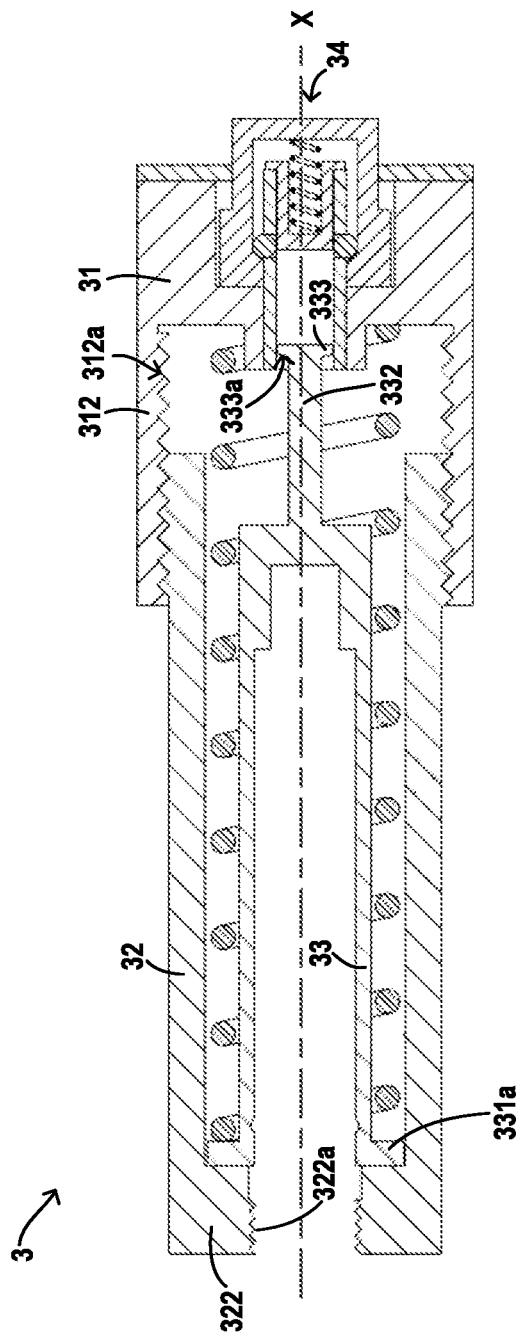
FIG. 11 is a section view of a needleless syringe body according to a preferred embodiment of the present disclosure.

FIG. 11 illustrates a preferred embodiment of a needleless syringe body 3, which is used together with the injection head 2 and the vial 1 as described above. As shown in FIG. 11, the needleless syringe body 3 includes a base 31, an outer housing 32 and an inner push rod 33. The base 31 includes a forward opening. The outer housing 32 is provided with a rearward opening and mounted at the front end of the base 31 such that a receiving space is formed between the base 31 and the outer housing 32. The outer housing 32 is further provided with a front opening for fixedly mounting the medicine barrel 21. The inner push rod 33 is disposed within the receiving space and is provided a forward opening. The vial 1 can be received within the inner push rod 33 and moves along with the inner push rod 33. The piston rod 22 is fixedly mounted at the forward opening.

Figure 14:
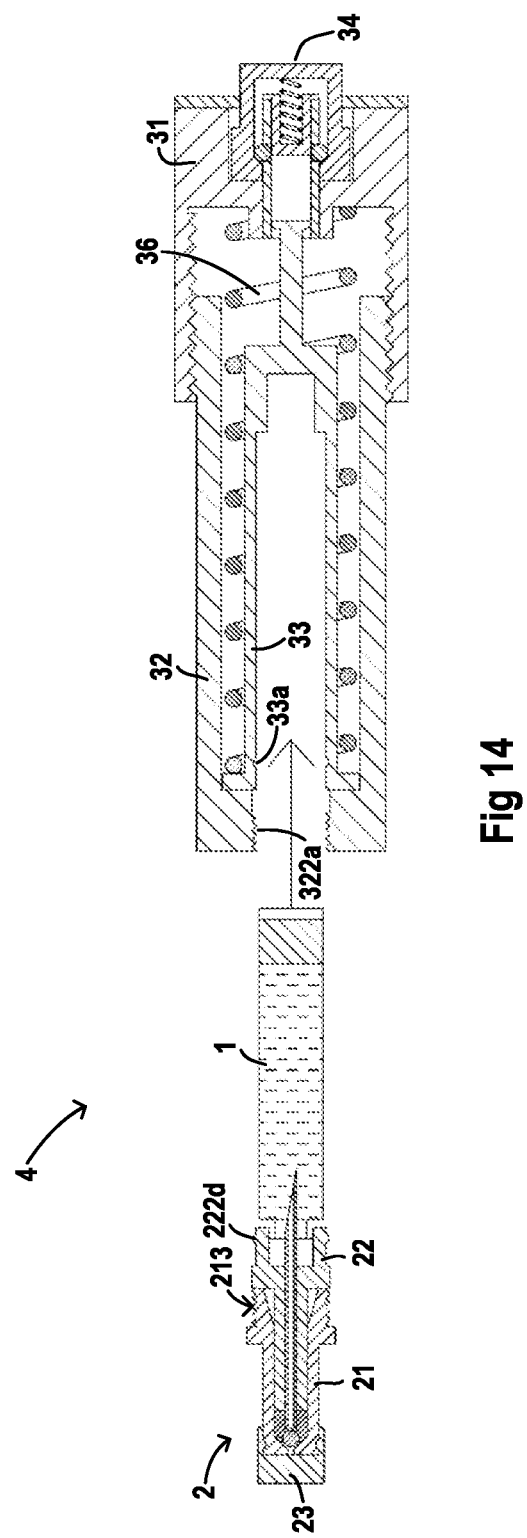
FIGS. 14-19 are section views of the needleless syringe when the injection head and the vial are mounted to a needleless syringe body, and the needleless syringe is used in a medicine suctioning process and a needleless-injection process.

The connecting way of the components as mentioned above may be of multiple types. For example, a threaded connection may be provided between the outer housing 32 and the medicine barrel 21. Referring to FIG. 14, the outer surface of the rear portion of the medicine barrel 21 is provided thereon with medicine-barrel external threads 213, the front opening of the outer housing 32 is provided with in-housing internal threads 322a, and the medicine-barrel external threads 213 can cooperate with the in-housing internal threads 322a to secure the medicine barrel 21 and the outer housing 32 relative to each other. The medicine barrel 21 may be provided with a limiting flange 212 for engagement on the front end face of the outer housing 32.

The piston rod 22 may be cooperated with the inner push rod 33 in snap fit. Specifically, continuing with FIG. 14, the piston rod 22 at the outer surface is provided with a snap-fit protrusion 222d, the inner push rod 33 at the corresponding position is provided with a snap-fit recess 33a, and the snap-fit protrusion 222d is snap-fitted into the snap-fit recess 33a to secure the piston rod 22 relative to the inner push rod 33. The rear portion 222a of the piston rod 22 may be of a large radial size to match the inner push rod 33. Further, the space within the inner push rod 33 may be of a size adapted to the vial 1, and after the piston rod 22 is snap-fitted with the inner push rod 33, the vial 1 is adaptively disposed in the space which leaves no room for movement of the vial 1 relative to the inner push rod 33.

As such, throughout the medicine suctioning and injection process, the outer housing 32 is fixed relative to the medicine barrel 21, the inner push rod 33 is fixed relative to both of the vial 1 and the piston rod 22, but the outer housing 32, the inner push rod 33 and the base 31 are movable relative to one other. Therefore, the outer housing 32 can drive the medicine barrel 21 to move, and the inner push rod 33 can drive the vial 1 and the piston 221 to move.

Specifically, the outer housing 32 can move in an front-rear direction relative to the inner push rod 33 to drive the medicine barrel 21 to move in an front-rear direction relative to the vial 1 and the piston 22, thereby implementing medicine suction and injection. More specifically, during the medicine suctioning process (see FIG. 17), the inner push rod 33 is fixed relative to the base 31, and the outer housing 32 moves forwards relative to the inner push rod 33; during the injection process (see FIG. 19), the outer housing 32 is fixed relative to the base 31, and the inner push rod 33 moves forwards relative to outside inner push rod 33 outer housing 32. The specific medicine suction and injection process will be described below in detail.

Preferably, the needleless syringe body 3 further includes a locking mechanism 34 which is connected between the base 31 and the inner push rod 33 to lock the inner push rod 33 relative to the base 31 during the medicine suctioning process, and to unlock the same after medicine suction to cause the inner push rod 33 to move forwards relative to the outer housing 32.

Figure 12:
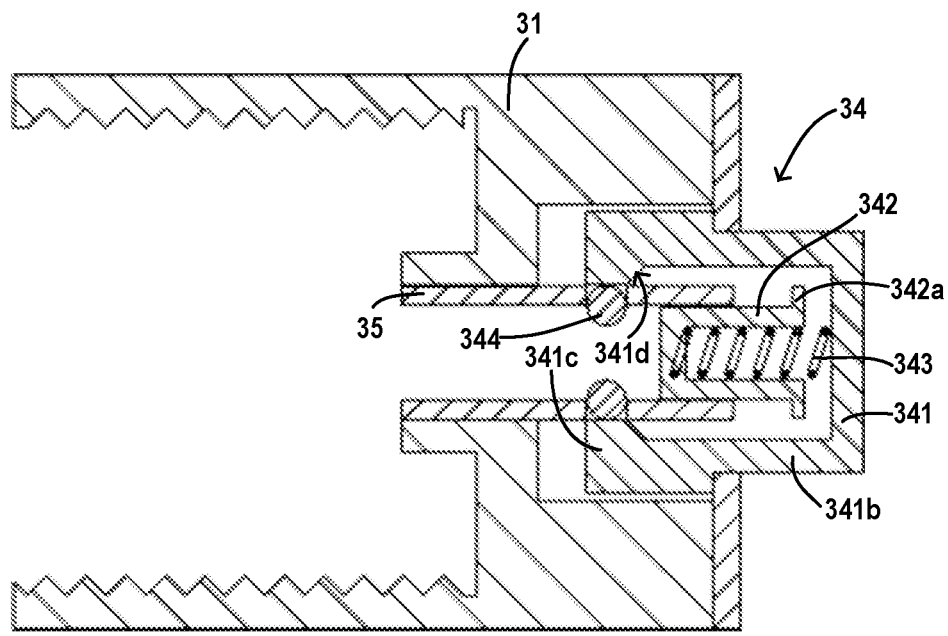
FIG. 12 is a section view of a rear end of the needleless syringe in FIG. 11, where a locking mechanism is in a locked state.
Figure 13:
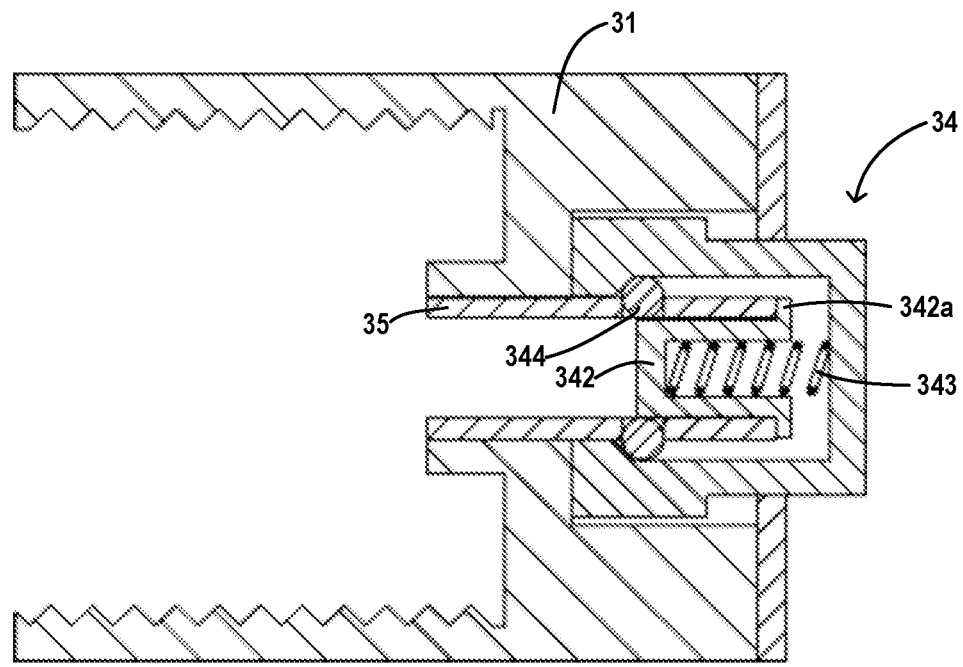
FIG. 13 is a further section view of the rear end of the needleless syringe in FIG. 11, where the locking mechanism is in a unlocked state.

FIGS. 12 and 13 illustrate a preferred embodiment of the locking mechanism 34, in which the inner push rod 33 is not shown. FIG. 12 shows a locked state of the locking mechanism 34 while FIG. 13 shows an unlocked state. FIGS. 16-19 illustrate a state where the inner push rod 33 is mated with the locking mechanism 34.

Figure 16:
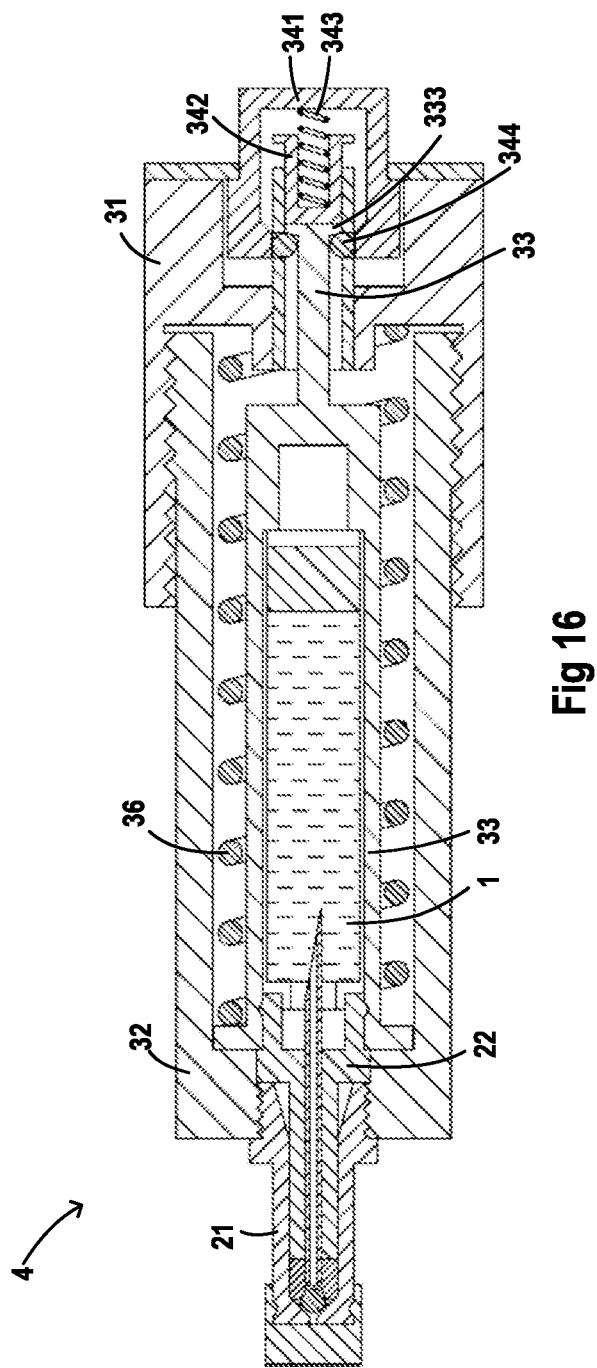

The rear end of the inner push rod 33 is provided with a rear end flange 333 protruding radially outwards (see FIG. 16) for mating with the locking mechanism 34. Referring to FIGS. 12, 13 and 16, the locking mechanism 34 includes a limiting member 344, button 341, spring receiving member 342 and button spring 343. The limiting member 344 in the locked state can abut against a front end face 333a of the rear end flange 333 to limit forward movement of the inner push rod 33; the button 341 is mounted at the rear end wall of the base 31 and protrudes rearwards relative to the base 31; the spring receiving member 342 is provided between the rear end face of the inner push rod 33 and the rear end wall of the button 341, which has a spring receiving chamber that opens rearwards; and the button spring 343 is disposed within the spring receiving chamber and can contact at its rear end with the button 341.

In this way, the button 341 can be pushed, and the button spring 343 and the spring receiving member 342 in turn are pushed to indirectly push the inner push rod 33 such that the rear end flange 333 of the inner push rod 33 can pass over the limiting member 344, causing the locking mechanism 34 to unlock the inner push rod 33. In other embodiments not shown, such members as the spring button 343, the spring receiving member 342, and the like may not be provided, and the button 341 directly pushes the inner push rod 33, causing the locking mechanism 34 to unlock the inner push rod 33.

Figure 17:
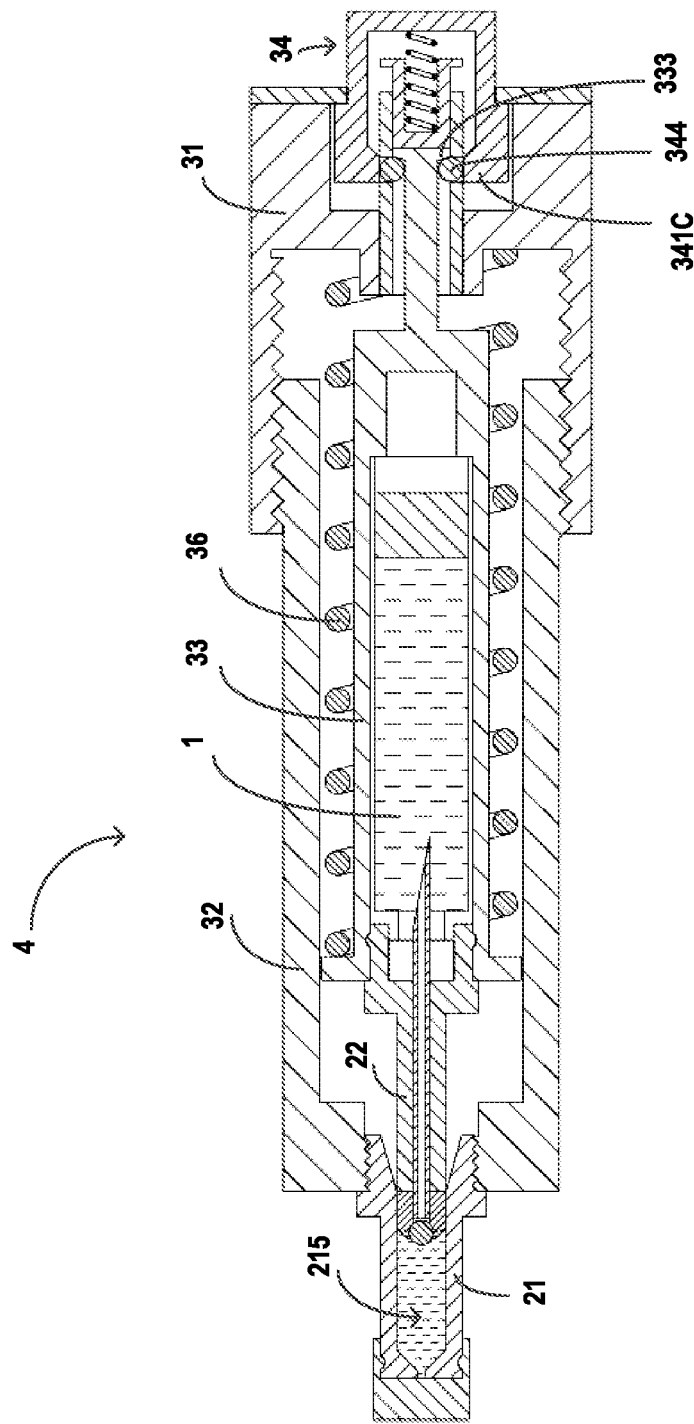
Figure 18:
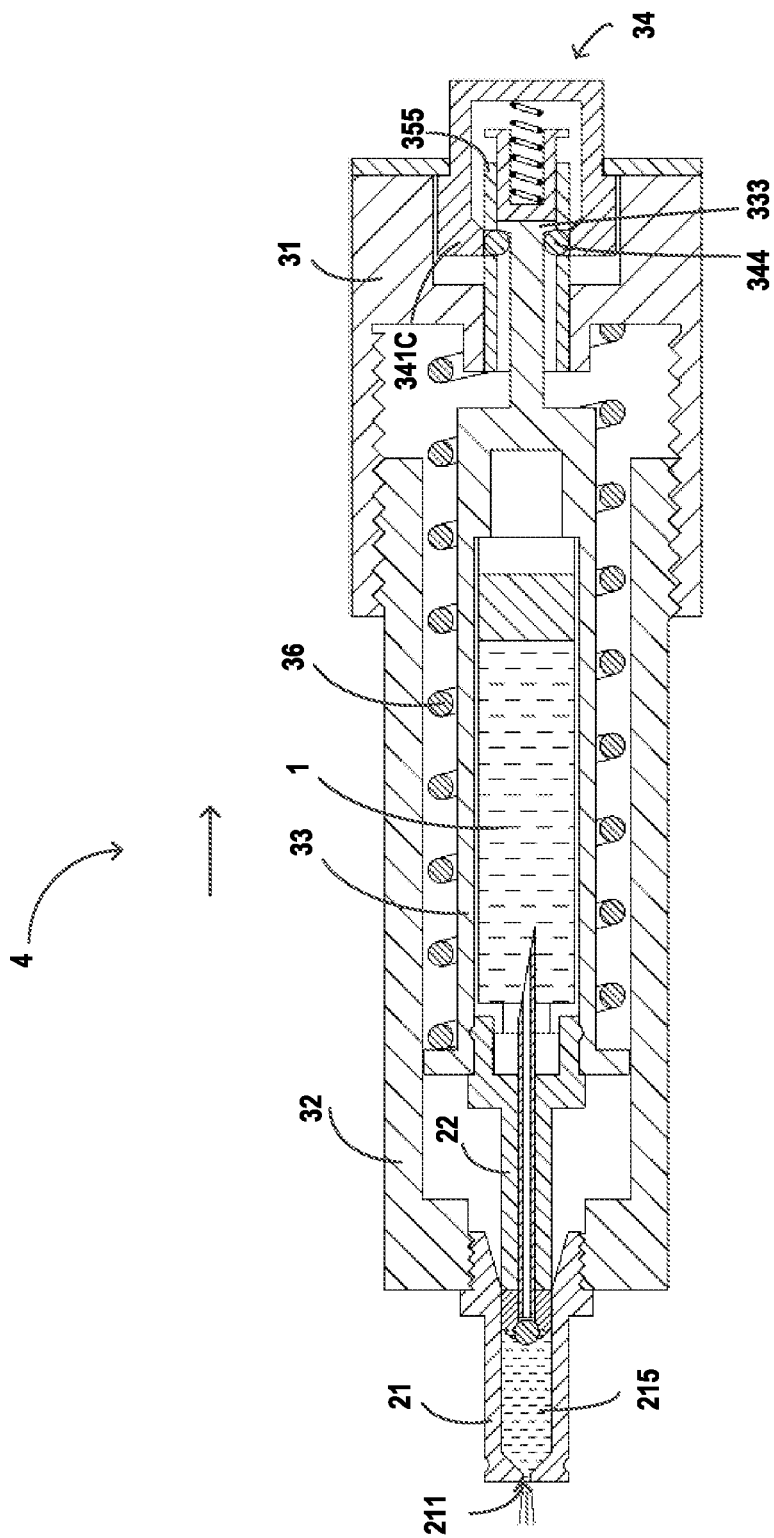
Figure 19:
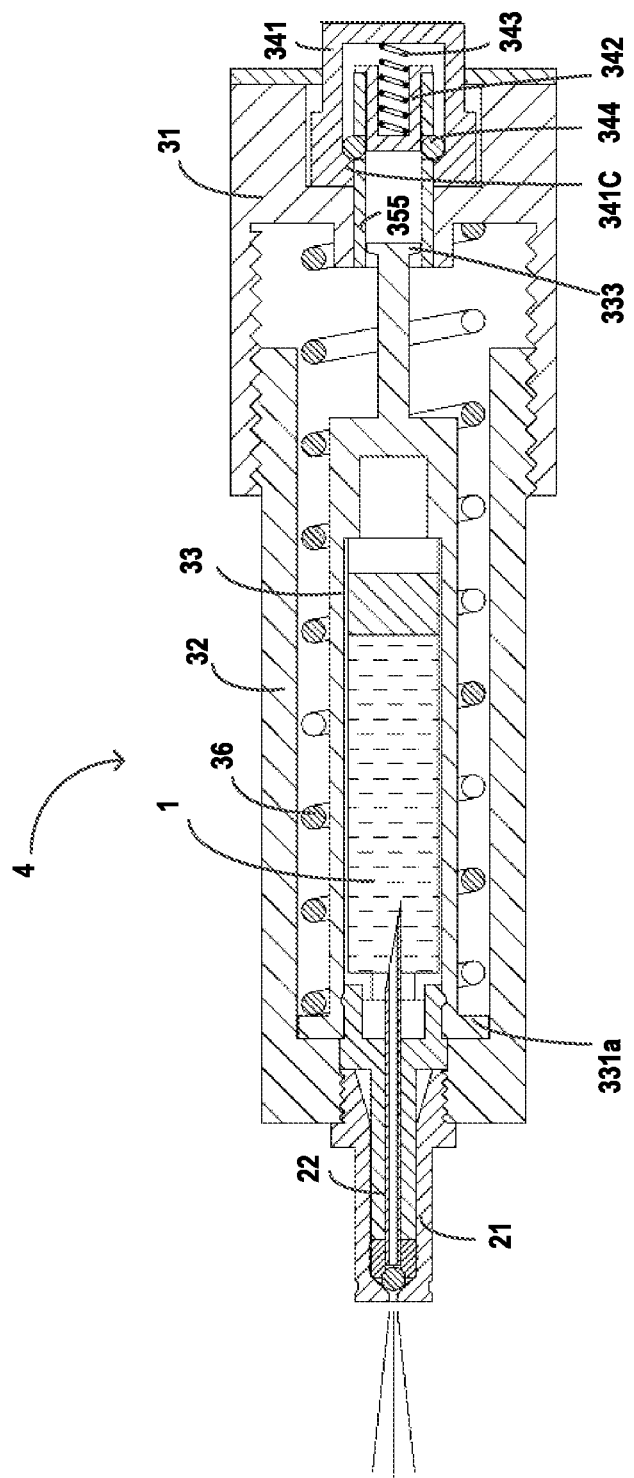

Preferably, continuing with FIGS. 12-19, the button 341 includes a rear end wall and a sidewall 341b extending around the axis X and forwards from the rear end wall, the sidewall 341b at the front end is provided with a protrusion portion 341c protruding towards the axis of the needleless syringe body 3, and the limiting member 344 is movable relative to the button 341 in a radial direction about the axis. Wherein, in the locked state as shown in FIGS. 12 and 16-18, the protrusion portion 341c abuts against the radial outside of the limiting member 344 to limit its radial outward movement. As being unable to move radially outwards, the limiting member 344 can stably abut against the front end face 333a of the rear end flange 333 of the inner push rod 33 to lock the inner push rod 33; when the button 341 is pushed, the protrusion portion 341c moves forwards relative to the limiting member 344 to release its radial limit, and the limiting member 344 thus can move radially outwards to disengage from the front end face of the rear end flange 333 of the inner push rod 33, thereby unlocking the inner push rod 33. FIGS. 13 and 19 show the state after unlocking the locking mechanism 34.

More preferably, the limiting member 344 may be two spheres disposed symmetrically about the axis. The rear end face 34d (see FIG. 12) of the protrusion portion 341c and the front end face 333a (see FIG. 11) of the rear end flange 333 of the inner push rod 33 are both slopes, and the limiting member 344 can be in rolling contact with the slopes during the unlocking process, such that a user can achieve unlocking only upon application of a small thrust onto the button 341.

In other embodiments not shown, other locking mechanism 34 may also be provided. For example, the locking mechanism 34 may be an electromagnet. After the injection head 2 and the vial 1 are mounted within the needleless syringe body 3, the electromagnet may be powered on to lock the inner push rod 33 and then medicine suction is performed. After medicine suction is completed, the electromagnet may be powered off, thereby losing magnetism. At this time, the inner push rod 33 can move forwards relative to the outer housing 32 to implement injection.

Preferably, referring to FIGS. 11 and 14-19, the needleless syringe body 3 further includes a resilient actuation mechanism located between the base 31 and the inner push rod 33. The resilient actuation mechanism is configured to be operated before injection for energy accumulation and then release the energy to actuate the inner push rod 33 forwards through a resilient force, and the inner push rod 33 then drives the piston rod 22 to compress the medicine liquid within the medicine liquid receiving chamber 215 of the medicine barrel 21 to implement injection. In other embodiments not shown, the resilient actuation mechanism may be a pneumatic spring, airbag, or the like.

Specifically, the inner push rod 33 at the front end is provided with a front end flange 331a protruding radially outwards, and the resilient actuation mechanism includes an actuation spring 36 between the front end flange 331a and the base 31, which is sleeved outside the inner push rod 33.

Preferably, threads are provided between the outer housing 32 and the base 31, and the outer housing 32 can move rearwards relative to the base 31 by means of threaded contact. Specifically, referring to FIG. 11, the base 31 includes a rear end portion and a base sidewall 312 extending forwards from the rear end portion, and the base sidewall 312 at its inner surface is provided with internal threads 312a. The outer housing 32 at its rear outer surface is provided with external threads. Through cooperation of the internal and external threads, the outer housing 32 can stably compress the actuation spring 36 when moving rearwards relative to the base 31.

Also preferably, the respective portions of the outer housing 32 and the inner push rod 33 facing the vial 1 in the radial direction may be configured to be at least partly transparent or hollow, making a volume of the medicine liquid within the vial 1 visible from outside.

FIGS. 14-20 show a process from mounting the needleless syringe 4 and the vial 1 until completing injection, which sequentially includes following main steps of: mounting, pressurized energy accumulating, medicine suctioning, and injecting. The respective steps will be sequentially described below with reference to the drawings.

FIG. 14 illustrates a schematic diagram of a process of mounting the injection head 2 and the vial 1 to the needleless syringe body 3. As shown therein, the piston rod 22 of the injection head 2 is first inserted into the vial 1, and the injection head 2 and the vial 1 then are mounted as a whole into the needleless syringe body 3. When the vial 1 enters the inner push rod 33 and moves rearwards until it cannot be moved further, the piston rod 22 and the inner push rod 33 are engaged with each other, and the medicine barrel 21 and the outer housing 32 are screwed through threads.

Figure 15:
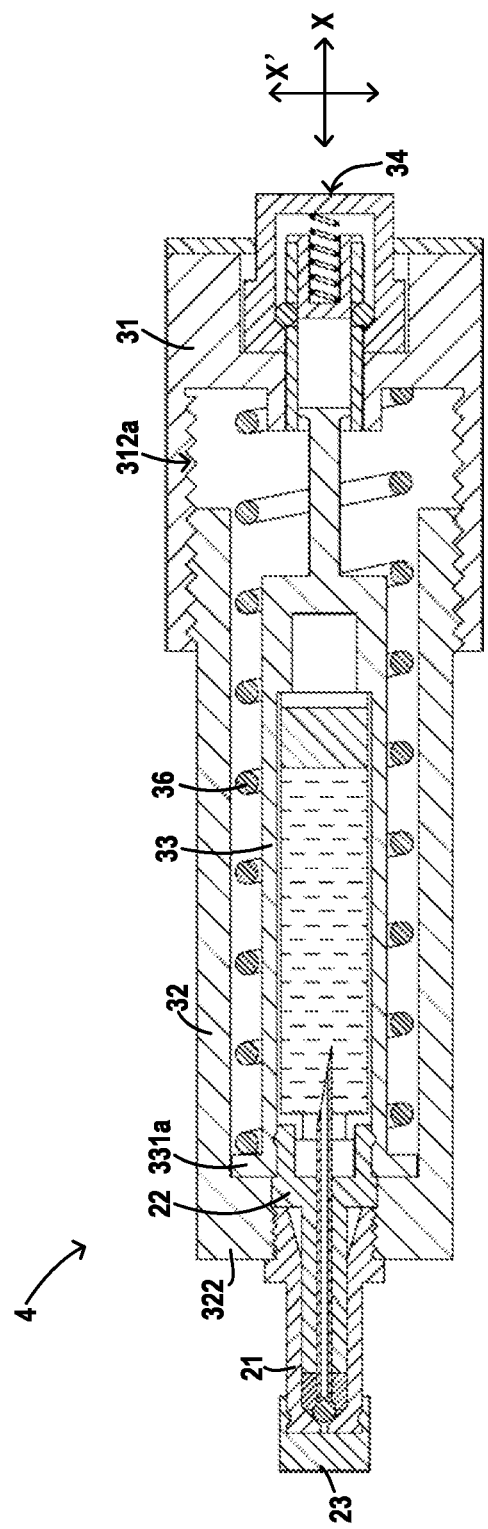

The state of each component after assembling is shown in FIG. 15, where the needleless syringe 4 is in a ready-to-use state. In this state, the medicine barrel 21 is fixed relative to the outer housing 32, the piston rod 22 and the vial 1 are fixed relative to the inner push rod 33, and the locking mechanism 34 is still at an initial state, which has not locked the inner push rod 33 relative to the base 31 yet.

The process as shown in FIGS. 15-16 is a pressurized energy accumulation process for the actuation spring 36. Specifically, the outer housing 32 is rotated to move forwards relative to the base 31 (which is achieved through thread fit therebetween), and the front end 322 of the outer housing 32 can exert a force on the front end flange 331a of the inner push rod 33 thus to drive the inner pusher rod 33 to move rearwards simultaneously. When the outer housing 32 is screwed threadedly relative to the base 31, the rear end flange 333 of the inner push rod 33 engages with the rear portion of the limiting member 344 such that the limiting member 344 abuts against the front surface of the rear end flange 333 to lock the inner push rod 33. In the course, the actuation spring 36 is compressed to accumulate energy for the final injection step.

The process as shown in FIGS. 16-17 is a medicine suctioning step. Specifically, the outer housing 32 is rotated to move forwards relative to the base 31 (which is achieved through thread fit therebetween), while the inner push rod 33 is fixed relative to the base 31 as being locked by the locking mechanism 34. In other words, during this process, the outer housing 32 moves forwards relative to the inner push rod 33. Since the medicine barrel 21 is fixed relative to the outer housing 32 and the vial 1 and the piston rod 22 are fixed relative to the inner push rod 33, the medicine 21 moves forwards relative to the vial 1 and the piston rod 22. Furthermore, since the injection micropore 211 of the medicine barrel 21 is closed by the cap 23, the medicine liquid receiving chamber 215 is formed within the medicine barrel 21 when the medicine barrel 21 moves forwards relative to the piston rod 22. Due to a small pressure within the medicine receiving chamber 215, the liquid within the vial 1 is suctioned into the medicine liquid receiving chamber 215 via the medicine liquid channel 222c within the piston rod 22, thereby completing medicine suctioning.

The step as shown in FIG. 18 is an injection preparation step prior to the medicine suctioning step and the injection step, with the purpose of discharging gas probably mixed out of the medicine barrel 21 before injection. This step includes first removing the cap 23 to expose the injection micropore 211 and then rotating the outer housing 32 to move the same slightly rearwards relative to the base 31, where the inner push rod 33 and the piston rod 22 are kept fixed relative to the base 31. In the circumstance, the medicine barrel 21 actually moves slightly rearwards relative to the piston rod 22 to make the piston rod 22 gently compress the medicine liquid chamber 215 within the medicine barrel 21, such that the gas within the medicine liquid receiving chamber 215 can be discharged from the injection micropore 211 as an effect of pressure.

The process as shown in FIG. 19 is an injection step. At this step, the outer housing 32 and the medicine barrel 21 are fixed relative to the base 31, and the inner push rod 33, the vial 1, and the piston rod 22 move forwards relative to the base 31 to compress the medicine liquid within the medicine liquid receiving chamber 215 via the piston rod 22, thereby completing injection. Specifically, the injection step further includes an unlocking step and a resilient actuation step.

If injection is required, the button 341 at the rear end of the base 31 is pressed to move forwards. In the case, the protrusion portion 341c at the front end of the button 341 moves forwards to release radial restrictions on the limiting member 344 such that the limiting member 344 can move radially outwards to unlock the rear end flange 333 of the inner push rod 33. In addition, along with the forward movement of the button 341, the inner push rod 33 is driven to move forwards via the button spring 343 and the spring receiving portion. The inner push rod 33 passes over the limiting member 344, causing the locking mechanism 34 to unlock the inner push rod 33.

After unlocking, the inner push rod 33 can move forwards relative to the base 31. At this time, the pressurized actuation spring 36 applies a large thrust to the front end flange 331a of the inner push rod 33 such that the inner push rod 33 drives the piston rod 22 to move forwards to push the medicine liquid within the medicine liquid receiving chamber 215 and thus eject the medicine liquid out of the injection micropore 211.

As can be seen from the above-mentioned steps, the front end flange 331a of the inner push rod 33 is provided for at least two purposes: one is that, at the pressurized energy accumulation step, a force is applied to the front end flange 331a of the inner push rod 33 when the outer housing 32 moves rearwards relative to the base 31, to drive the inner push rod 33 to move rearwards along therewith relative to the base 31 until reaching the locked position where the inner push rod 33 is locked by the locking mechanism; and the other is that, at the injection step, as being pressed between the base 31 and the front end flange 331a of the inner push rod 33, the actuation spring 36 applies a thrust to the front end flange 331a to push the inner push rod 33 forwards to complete injection.

Figure 20:
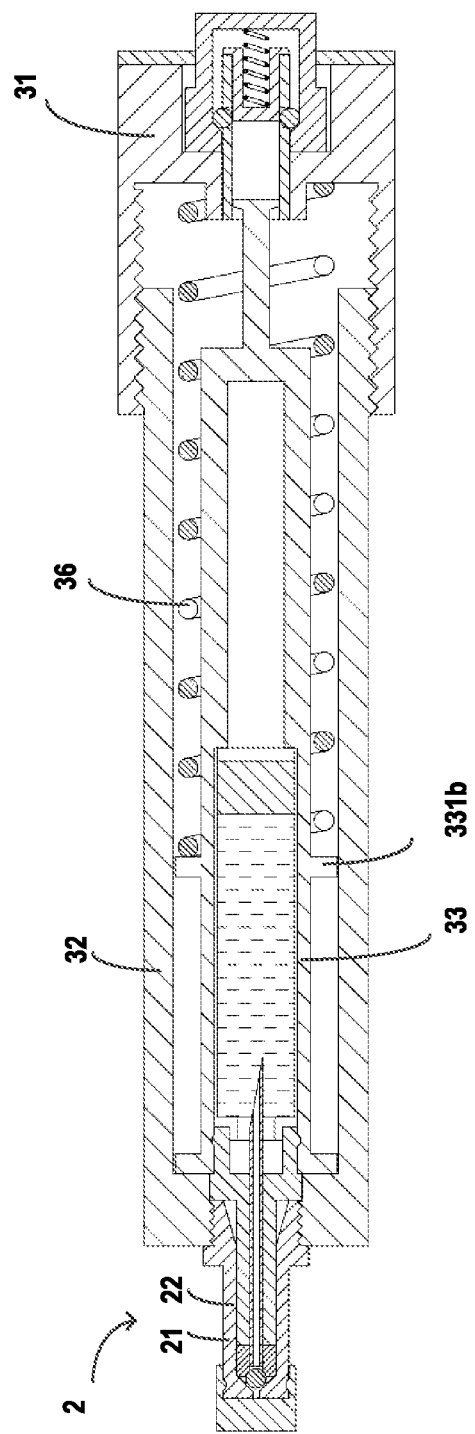
FIG. 20 is a section view of an alternative solution of the needleless syringe in FIGS. 14-19.

FIG. 20 shows a variation of the aforesaid embodiment. In the needleless syringe as shown in FIG. 20, the inner push rod 33 is provided with a middle flange 331b, and the actuation spring 36 is pressed between the base 31 and the middle flange 331b. In order to ensure that the actuation spring 36 is long enough to provide a sufficient actuation force, the inner push rod 33 is prolonged properly. Such arrangement prevents the actuation spring 36 from sheltering the vial 1 to make the volume within the vial visible from outside.

Figure 21:
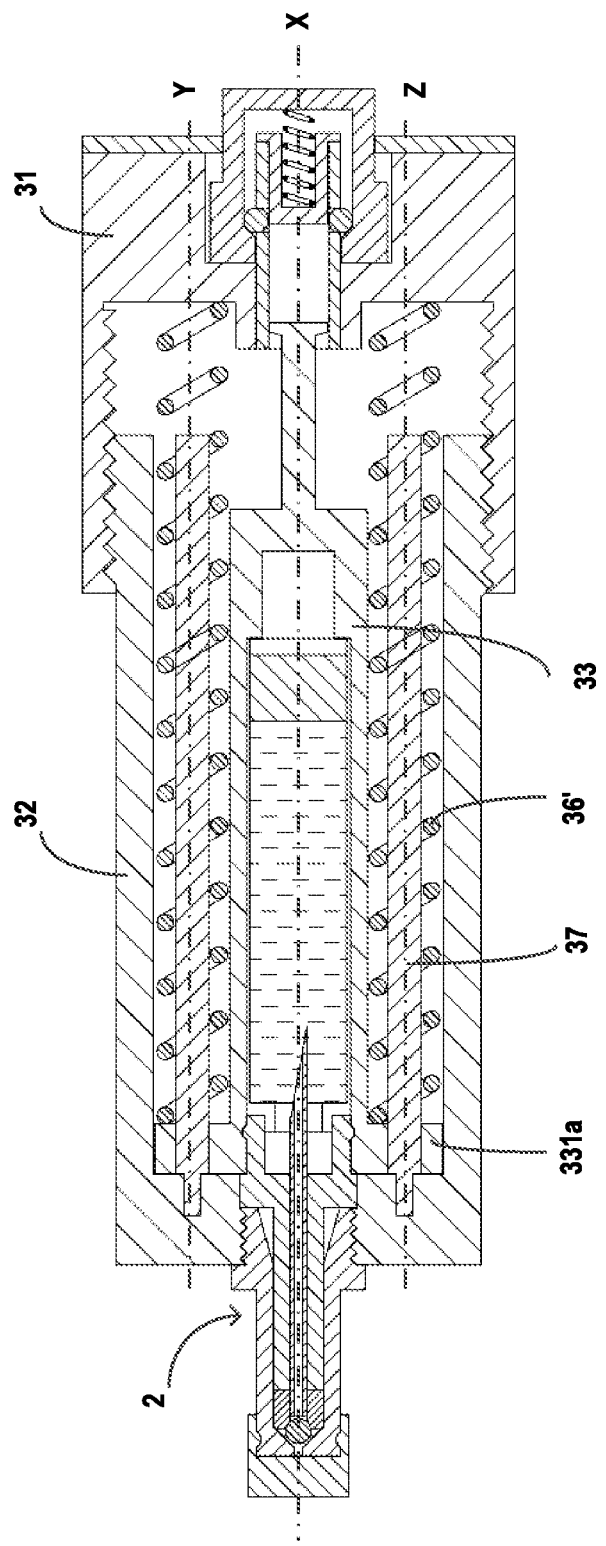
FIG. 21 is a section view of a further alternative solution of the needleless syringe in FIGS. 14-19.

FIG. 21 shows a further variation of the aforesaid embodiment. In the needleless syringe as shown in FIG. 21, a spring shaft 37 is fixedly connected at the front end flange 331a of the inner push rod 33 of the needleless syringe body 3, which extends rearwards from the front end flange 331a along a direction parallel to the axis X and is sheathed in the actuation spring 36. Preferably, in order to apply a uniform thrust onto the inner push rod 33, a plurality of spring shafts 37 may be provided, each being sheathed in an actuation spring 36. The respective spring shafts 37 are arranged around the inner push rod 33 evenly or unevenly. In FIG. 21, the needleless injection body 3 is provided therein with two spring shafts 37 which respectively extend along a direction Y and a direction Z being symmetrical with respect to the axis X.

Other components of the needleless syringe as shown in FIGS. 20-21 are arranged similarly as those in FIGS. 14-19, and the description thereon is omitted here.

Figure 22:
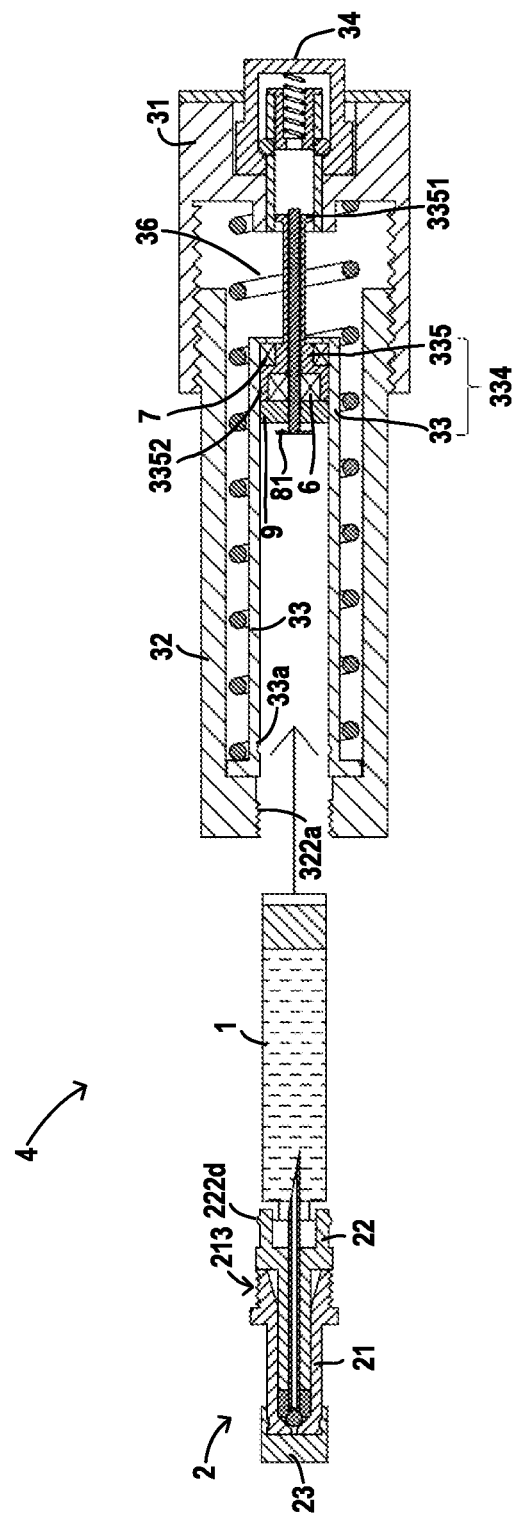
FIGS. 22-28 are section views of a needleless syringe when an injection head and a vial are mounted to a needleless syringe body, and the needleless syringe is used in a medicine suctioning process and a needleless-injection process, according to a further preferred embodiment.

FIGS. 22-28 are schematic diagrams of cooperative use of the injection head 2 and the needleless syringe body according to a further embodiment. As shown in FIG. 22, the needleless syringe body 3 includes a base 31, an outer housing 32, and an inner push rod system 334. Wherein, the base 31 includes a forward opening, the outer housing 32 includes a rearward opening and is mounted at the front end of the base 31 to form a receiving space between the base 31 and the outer housing 32, and the outer housing 32 is provided with a front opening for fixedly mounting the medicine barrel 21. The inner push rod system 334 includes an inner push rod 33 disposed within the receiving space and having a forward opening. The via 1 can be received within the inner push rod 33 and move along with the inner push rod 33, and the piston rod 22 is fixedly mounted at the forward opening.

Preferably, the respective portions of the outer housing 32 and the inner push rod 33 facing the vial 1 in the radial direction can be configured to be at least partly transparent or hollow, to make the volume of the medicine liquid within the vial 1 visible from outside.

The connection relation among the above-mentioned components may be of multiple types. For example, a threaded connection may be provided between the outer housing 32 and the medicine barrel 21. Referring to FIG. 22, the outer surface of the rear portion of the medicine barrel 21 is provided thereon with medicine-barrel external threads 213, the front opening of the outer housing 32 is provided with in-housing internal threads 322a, and the medicine-barrel external threads 213 can cooperate with the in-housing internal threads 322a to fix the medicine barrel 21 and the outer housing 32 relative to each other. The medicine barrel 21 may be provided with a limiting flange 212 for engagement on the front end face of the outer housing 32.

The piston rod 22 may be cooperated with the inner push rod 33 in snap fit. Specifically, continuing with FIG. 22, the piston rod 22 at the outer surface is provided with a snap-fit protrusion 222d, the inner push rod 33 at the corresponding position is provided with a snap-fit recess 33a, and the snap-fit protrusion 222d is snap-fitted into the snap-fit recess 33a to secure the piston rod 22 relative to the inner push rod 33. The rear portion 222a of the piston rod 22 may be of a large radial size to match the inner push rod 33. Further, the space within the inner push rod 33 may be of a size adapted to the vial 1, and after the piston rod 22 is snap-fitted with the inner push rod 33, the vial 1 is adaptively disposed in the space which leaves no room for movement of the vial 1 relative to the inner push rod 33.

As such, throughout the medicine suctioning and injection processes, the outer housing 32 is fixed relative to the medicine barrel 21, the inner push rod 33 is fixed relative to both of the vial 1 and the piston rod 22. But the outer housing 32, the inner push rod 33 and the base 31 are movable relative to one other in the axis direction. Therefore, the outer housing 32 can drive the medicine barrel 21 to move, and the inner push rod 33 can drive the vial 1 and the piston 221 to move.

Specifically, the outer housing 32 can move in an anterior-posterior direction relative to the inner push rod system to drive the medicine barrel 21 to move in an front-rear direction relative to the vial 1 and the piston 22, thereby implementing medicine suction and injection. More specifically, during the medicine suctioning process (see FIG. 25), the inner push rod 33 is fixed relative to the base 31, and the outer housing 32 moves forwards relative to the inner push rod 33; during the injection process (see FIG. 27), the outer housing 32 is fixed relative to the base 31, and the inner push rod system 334 moves forwards relative to outside inner push rod 33. The specific medicine suction and injection process will be described below in detail.

Preferably, the needleless syringe body 3 further includes a locking mechanism 34 which is connected between the base 31 and the inner push rod system 334 to lock the inner push rod system 334 relative to the base 31 in the axial direction during the medicine suctioning process, and to unlock the same after medicine suction, causing the inner push rod system 334 to move forwards relative to the outer housing 32.

Preferably, the outer housing 32 and the base 31 are connected in thread fit, to implement conversion of the relative rotation of the two into relative linear movement. Specifically, referring to FIG. 8, the base 31 includes a rear end portion and a base sidewall 312 extending forwards from the rear end portion, and the base sidewall 312 at its inner surface is provided with internal threads 312a. The outer housing 32 at its rear outer surface is provided with external threads. With the cooperation of the internal and external threads, the rotation of the outer housing 32 relative to the base 31 can lead to front-rear movement relative to each other.

In order to accelerate the medicine suctioning rate in the medicine suctioning process, the needleless syringe body 3 further includes a medicine supply push rod 8 mounted at the rear end of the inner push rod 33, and a front end of the medicine supply push rod 8 can be in contact with the cork of the vial. In order to transmit the relative movement between the outer housing 32 and the base 31 to the medicine supply push rod 8, the needleless syringe body 3 further includes transmission means. A part of the transmission means is connected to the medicine supply push rod 8 while the other part of the transmission means is connected directly or indirectly to the base 31 or the outer housing 32, to transmit specified relative movement between the base 31 and the outer housing 32 to the medicine supply push rod 8. During the medicine suctioning process, the base 31 or the outer housing 32 drives, via the transmission means, the medicine supply push rod 8 to push the cork 12 forwards relative to the body of the vial 1 and thus compress the space within the vial 1.

Preferably, the inner push rod system 334 further includes a transmission rod 335 cooperating with the transmission means, which is connected at a front end to the transmission means and engaged at a rear end 3351 with the locking mechanism 34. When locked by the locking mechanism 34, the transmission rod 335 is fixed relative to the base 31 in the rotational direction. A thrust bearing 7 is mounted between the transmission rod 335 and the inner push rod 33.

It can be seen that, in the present embodiment, the transmission means is indirectly connected to the base 31 via the transmission rod 335, so as to transmit the specified movement of the base 31 to the transmission means. However, in other embodiments not shown, there may not be a transmission rod 335, and the base 31 may be directly connected to the transmission means.

Preferably, the axes of the transmission rod 335 and the medicine supply push rod 8 are the axis X of the needleless syringe body. A receiving chamber 332 of the medicine supply push rod (see FIG. 29) extending along the axis X may be disposed within the transmission rod 335, within which the medicine supply push rod 8 is mounted adaptively. The outer surface of the medicine supply push rod 8 is a threaded surface while the medicine supply push rod receiving chamber 332 has a smooth surface, such that the medicine supply push rod 8 can move along the axis direction within the medicine supply push rod receiving chamber 332.

In the present embodiment, during the medicine suctioning process, the base 31 rotates to move forwards relative to the outer housing 32, and the transmission means includes transmission means for rotational movement accordingly. The base 31 transmits the rotational movement via the transmission means for rotational movement to the medicine supply push rod 8 to drive the latter to rotate along therewith. In order to convert the rotational movement of the medicine supply push rod 8 into a linear movement and thus push the cork 12 forwards, a movement conversion mechanism is fixedly provided within the receiving space of the inner push rod 33. A part of the movement conversion mechanism is engaged with the medicine supply push rod 8 while the other part is engaged with the inner push rod 33, for conversion of the rotational movement of the medicine supply push rod 8 along with the base 31 relative to the outer housing (i.e., relative to the inner push rod 33) into a linear movement relative to the outer housing 32 along the axis direction.

The movement conversion mechanism, for example, may include a nut member 9 for engagement with the medicine supply push rod 8 in thread fit. In other embodiments not shown, the movement conversion mechanism may include other members capable of converting a relative rotational movement into a linear movement.

More preferably, the transmission means for rotational movement includes one-way transmission means for rotational movement. The one-way transmission means for rotational movement can only transmit one-way rotation of the transmission rod 335 to the medicine supply push rod 8. More specifically, when the outer housing 32 rotates along a first rotational direction relative to the base 31 to move forwards relative to the same, the one-way transmission means for rotational movement can transmit the rotational movement of the transmission rod 335 to the medicine supply push rod 8; in turn, when the outer housing 32 rotates in a direction opposite to the first rotational direction relative to the base 31 to move rearwards relative to the same, the one-way transmission means for rotational movement can transmit the rotational movement of the transmission rod 335 to the medicine supply push rod 8.

Figure 30A:
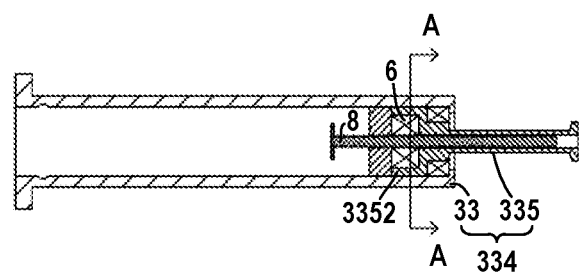
FIG. 30A is a section view of the structure in FIGS. 22-28 where an inner push rod system, a nut member and a one-way bearing are in an assembled state.
Figure 30B:
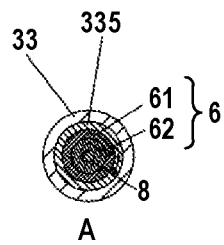
FIG. 30B is a schematic diagram cut along an A-A axis from FIG. 30A.

The one-way transmission means for rotational movement, for example, includes a one-way bearing. As shown in FIGS. 30A-30B, an outer ring 61 of the one-way bearing 6 is fixedly connected to the transmission rod 335, and an inner ring 61 of the one-way bearing 6 is fixedly connected to the medicine supply push rod 8 in the rotational direction. On the contact surfaces of the inner ring 62 and the medicine supply push rod 8, for example, a guide rod or keyway extending along the direction of the axis X may be provided to limit the relative rotation between the inner ring 62 and the medicine supply push rod 8, without restricting the relative linear movement therebetween in the axis direction.

In the medicine suctioning process, the base 31 is rotated relative to the outer housing 32 to move the outer housing 32 forwards relative to the base 31. During the rotational movement in the relative rotational direction, the outer ring 61 of the one-way bearing 6 can transmit the rotational movement to the inner ring 62, so as to drive the medicine supply push rod 8 to rotate. The medicine supply push rod 8 rotates relative to the nut member 9 and thus moves forwards relative to the nut member 9 and further relative to the inner push rod 33 (at the time, the whole push rod system 334 is locked by the locking mechanism 34 in the axis direction), to push the cork 12 of the vial 1 and further cause the medicine liquid within the vial 1 to enter the medicine barrel 21.

The transmission rod 335 at the rear part is provided with a rear end 3351 (see FIG. 27) of the transmission rod 335 protruding radially outwards, which is formed in a flange structure and provided for cooperating with the locking mechanism 34. The locking mechanism 34 includes a limiting member 344, button 341, spring receiving member 342, and button spring 343. In a locked state, the limiting member 344 can abut against the front end face of the rear end 3351 (which is formed in a flange structure) of the transmission rod 335 to limit the forward movement of the transmission rod 335; the button 341 is mounted at the rear end wall of the base 31 and protrudes rearwards relative to the base 31; the spring receiving member 342 is disposed between the rear end face of the transmission rod 335 and the rear end wall of the button 341, which has a spring receiving chamber that opens rearwards; and the button spring 343 is disposed in the spring receiving chamber and configured to contact at its rear end with the button 341.

In this way, the button 341 can be pushed, and the button spring 343 and the spring receiving member 342 in turn are pushed to directly push the transmission rod 335. In the circumstance, the rear end 3351 (which is formed in a flange structure) of the transmission rod 335 can pass over the limiting member 344, causing the locking mechanism 34 to unlock the transmission rod 335. In other embodiment not shown, such members as the button spring 343, the spring receiving member 342, and the like may not be provided, and the button 341 can directly push the transmission rod 335, causing the locking mechanism 34 to unlock the transmission rod 335.

In the present embodiment, a movement limiting feature (not shown) is provided between the circumferential outer surface of the front end flange 331 of the inner push rod 33 and the circumferential inner surface of the outer housing 32. The movement limiting feature is configured to limit rotation of the inner push rod 33 relative to the outer housing 32 while permitting front-rear movement of the inner push rod 33 relative to the outer housing 32 along the axis direction. The movement limiting feature, for example, may be a keyway or guide rod extending along the axis direction and disposed on the circumferential outer surface of the front end flange 331 and the circumferential inner surface of the outer housing 32.

Owing to arrangement of the movement limiting feature, in the pressurized and medicine suctioning processes, the inner push rod 33 can rotate along with the outer housing 32. However, when the inner push rod system 334 is wholly locked by the locking mechanism 34, the inner push rod 33 can only rotate along with the outer housing 32, being unable to move linearly.

The connection relation between the inner push rod 33 and the transmission rod 335 is of a specified type. Specifically, the circumferential outer surface of a transmission rod cooperating unit 3352 at the front end of the transmission rod 335 contacts and cooperates with the circumferential inner surface of the inner push rod 33. There is a large sliding friction therebetween (for example, the two have rough contact surfaces). If one is not subjected to an external force, it rotates along with the other, and if both are subjected to an external force, the two rotate relative to each other.

Specifically, when the transmission rod 335 is not locked by the locking mechanism 34, the transmission rod 335 can rotate along with the inner push rod 33, for example, in the pressurized process, but the rotational direction is not the transmission direction of the one-way bearing 6. Therefore, at this time, the rotation of the outer ring 61 of the one-way bearing 6 is not transmitted to the inner ring 62. At this time, the medicine supply push rod 8 is driven by the nut member 9 (i.e., directly driven by the inner push rod 33) to move linearly, and no relative shift is generated between the medicine supply push rod 8 and the inner push rod 33. When the transmission rod 335 is locked by the locking mechanism 34, the transmission rod 335 can only rotate along with the locking mechanism 34. For example, in the medicine suctioning process, the transmission rod 335 and the base 31 are consistent in rotational direction, the inner push rod 33 is consistent with the outer housing 32, and there is relative rotation between the inner push rod 33 and the transmission rod 335. However, since the inner push rod system 334 is wholly locked by the locking mechanism 34, the inner push rod 33 only rotates relative to the transmission rod 335, without translating relative to the same.

FIGS. 22-28 illustrate a process from mounting the needleless syringe 4 and the vial 1 until completing injection. The process sequentially includes main steps of: mounting, pressurized energy accumulating, medicine suctioning, and injecting. Reference will be made below to the drawings to describe the respective steps sequentially.

FIG. 22 illustrates a schematic diagram of a process of mounting the injection head 2 and the vial 1 to the needleless syringe body 3. As shown therein, the piston rod 22 of the injection head 2 is first inserted into the vial 1, and the injection head 2 and the vial 1 are subsequently mounted as a whole into the needleless syringe body 3. When the vial 1 enters the inner push rod 33 and moves rearwards until it cannot be moved any longer, the piston rod 22 and the inner push rod 33 are engaged with each other, and the medicine barrel 21 and the outer housing 32 are screwed through threads.

Figure 23:
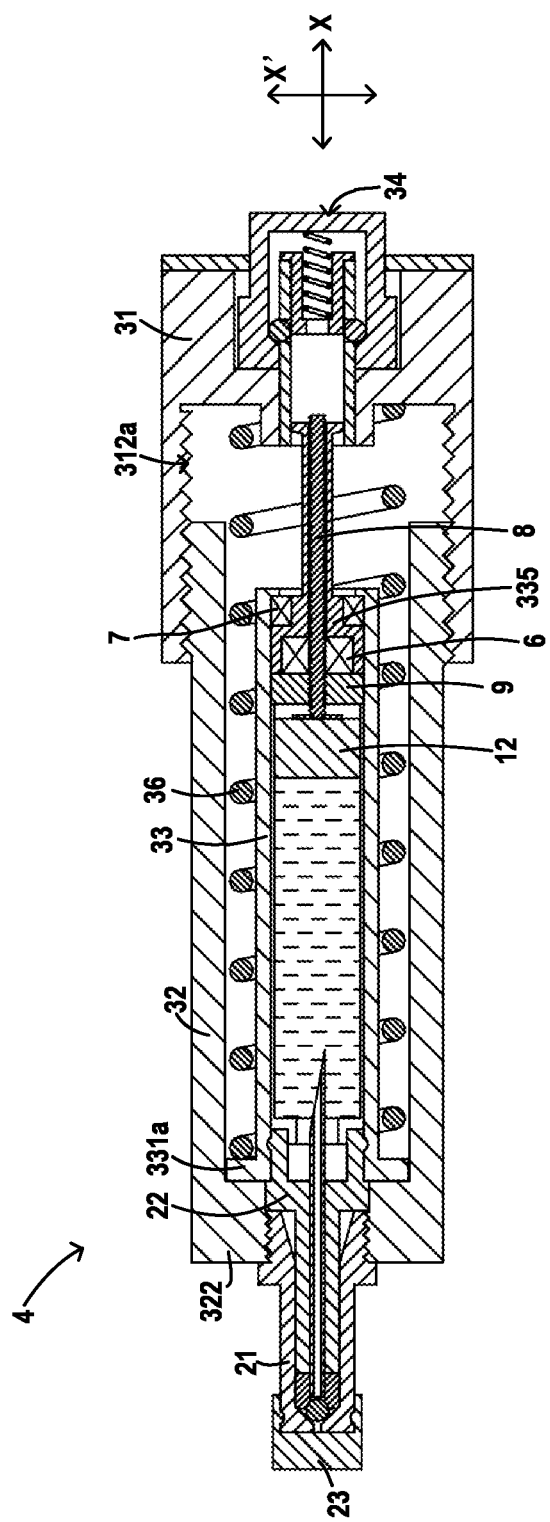

The state of each component after assembling is shown in FIG. 23, where the needleless syringe 4 is in a ready-to-use state. In the state, the medicine barrel 21 is fixed relative to the outer housing 32, the piston rod 22 and the vial 1 are fixed relative to the inner push rod 33, and the locking mechanism 34 is still at an initial state, which has not locked the inner push rod 33 relative to the base 31 yet.

Figure 24:
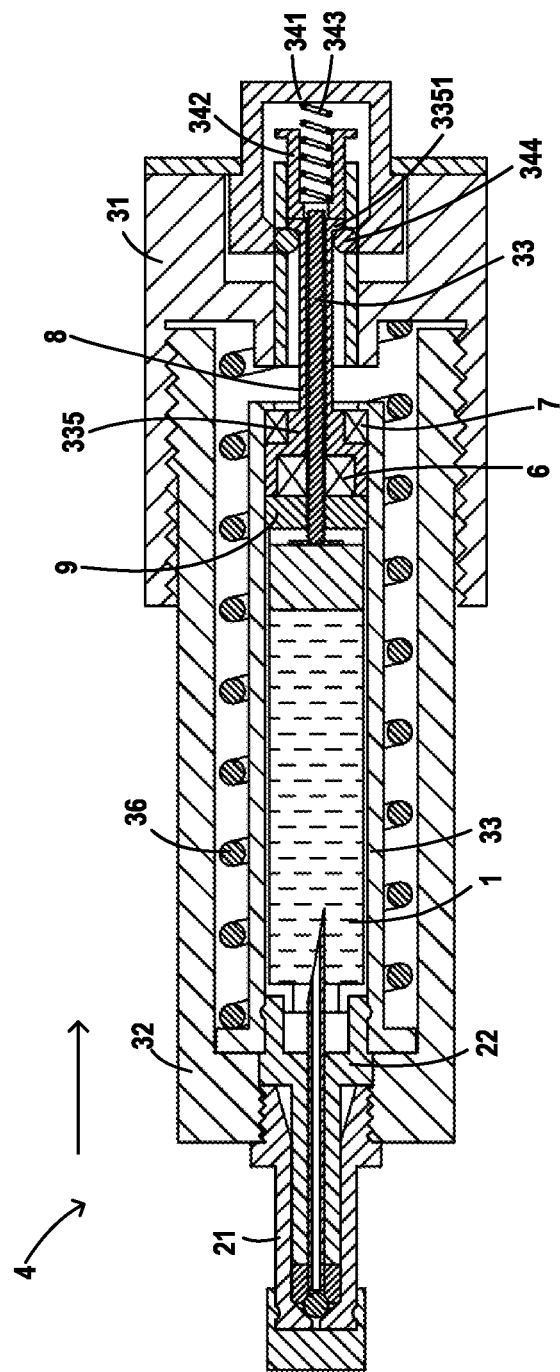

The process as shown in FIGS. 23-24 is a pressurized energy accumulation process for the actuation spring 36. Specifically, the outer housing 32 is rotated to move rewards relative to the base 31 (which is achieved through thread fit therebetween), and the front end portion 322 of the outer housing 32 can drive the inner push rod 33 to rotate along therewith while driving the inner push rod 33 to move rearwards. When the outer housing 32 is screwed threadedly relative to the base 31, the rear end 3351 (which is formed in a flange structure) of the transmission rod 335 is engaged with the rear portion of the limiting member 344, and at this time, the limiting member 344 abuts against the front surface of the rear end 3351 (which is formed in a flange structure) of the transmission rod 335 to lock the inner push rod system 334. In the course, the actuation spring 36 is compressed to accumulate energy for the final injection step.

Figure 25:
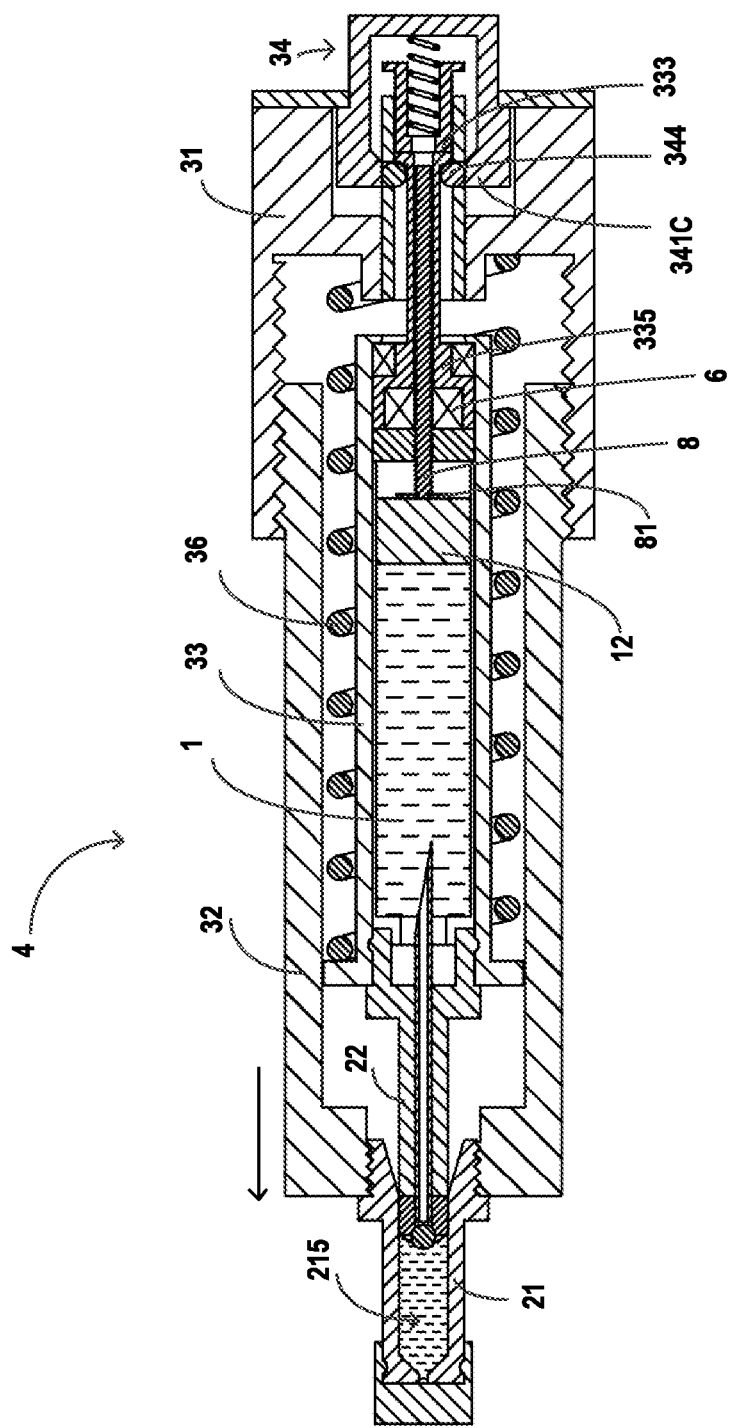

The process as shown in FIGS. 24-25 is a medicine suctioning step. Specifically, the outer housing 32 is rotated to move forwards relative to the base 31 (which is achieved through thread fit therebetween), while the inner push rod 33 is fixed relative to the base 31 in the axial direction as being locked by the locking mechanism 34. In other words, during this process, the outer housing 32 moves forwards relative to the inner push rod 33 (while rotating along therewith). Since the medicine barrel 21 is fixed relative to the outer housing 32 and the vial 1 and the piston rod 22 are fixed relative to the inner push rod 33, the medicine 21 moves forwards relative to the vial 1 and the piston rod 22. Furthermore, since the injection micropore 211 of the medicine barrel 21 is closed by the cap 23, the medicine liquid receiving chamber 215 is formed within the medicine barrel 21 when the medicine barrel 21 moves forwards relative to the piston rod 22. Due to a small pressure within the medicine receiving chamber 215, the liquid within the vial 1 can be suctioned into the medicine liquid receiving chamber 215 via the medicine liquid channel 222c within the piston rod 22, thereby completing medicine suctioning.

In the medicine suctioning process, the transmission rod 335 rotates along with the base 34 relative to the outer housing 32, and the transmission rod 335 transmits the rotational movement via the one-way bearing 6 to the medicine supply push rod 8. The medicine supply push rod 8 rotates relative to the nut member 9 and thus achieves forward movement relative to the nut member (i.e., relative to the inner push rod 33). The front end 81 (see FIG. 22) of the medicine supply push rod 8 pushes the cork 12 to further compress the space within the via, to make the medicine liquid flow into the medicine liquid receiving chamber 215.

Figure 26:
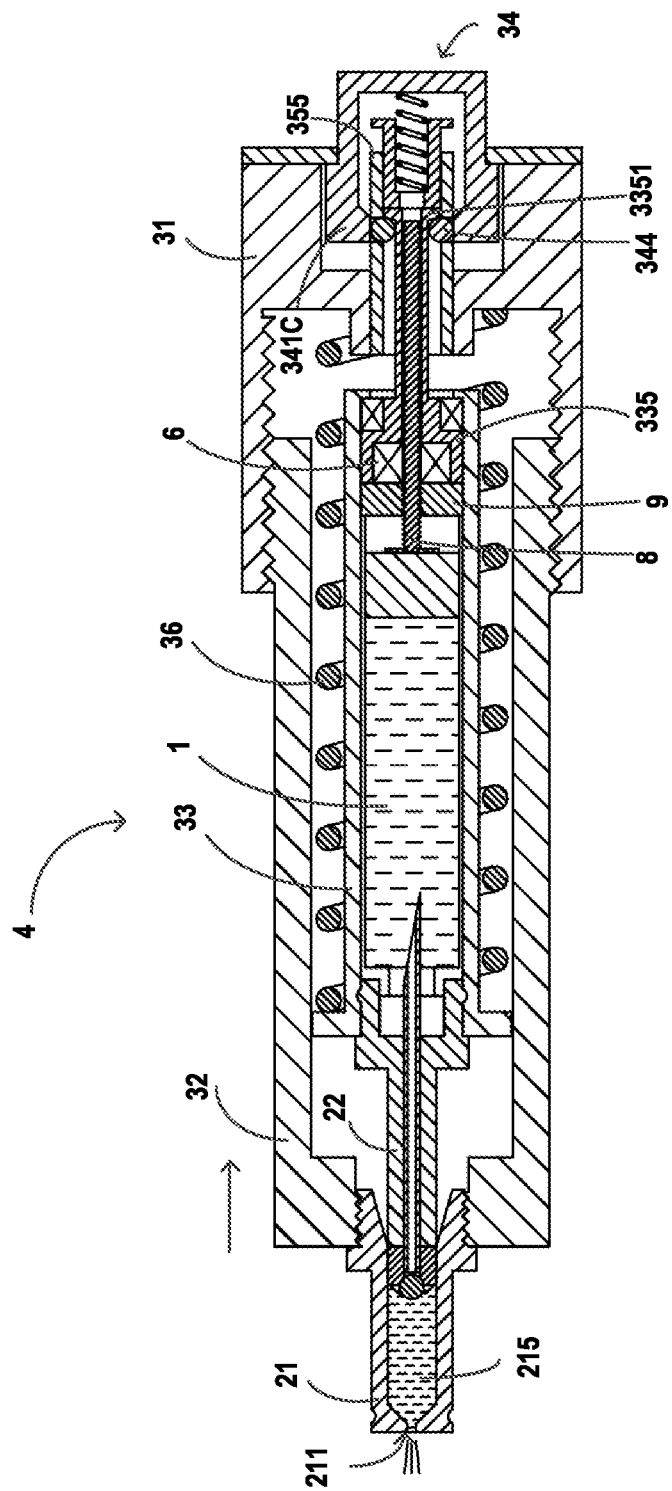

The step as shown in FIG. 26 is an injection preparation step prior to the medicine suctioning step and the injection step, with the purpose of discharging gas probably mixed out of the medicine barrel 21 before injection. This step includes first removing the cap 23 to expose the injection micropore 211 and then rotating the outer housing 32 to move the same slightly rearwards relative to the base 31, where the inner push rod 33 and the piston rod 22 are kept fixed relative to the base 31. In the circumstance, the medicine barrel 21 actually moves slightly rearwards relative to the piston rod 22 to gently compress the medicine liquid chamber 215 within the medicine barrel 21, such that the gas within the medicine liquid receiving chamber 215 can be discharged from the injection micropore 211 as an effect of pressure.

Figure 27:
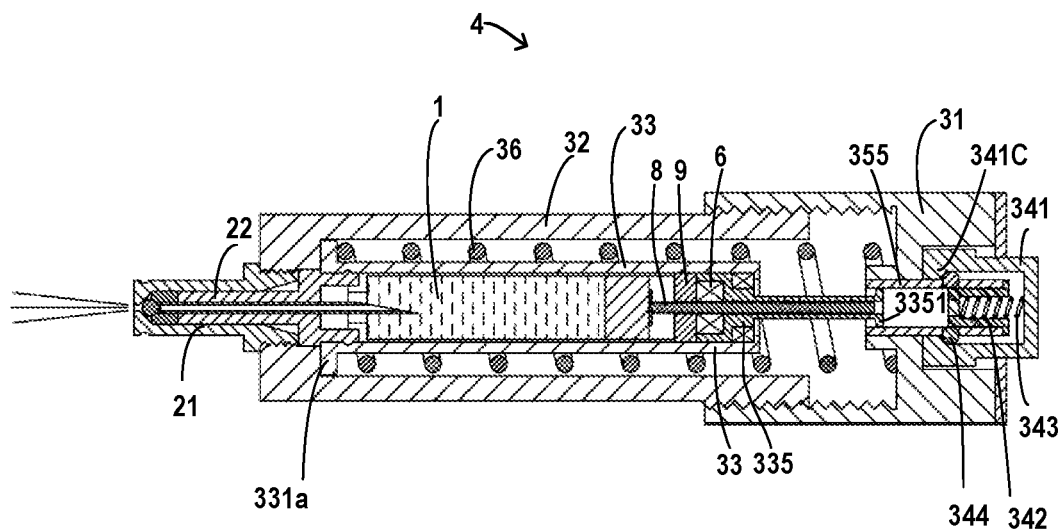

The process as shown in FIG. 27 is an injection step. At this step, the outer housing 32 and the medicine barrel 21 are fixed relative to the base 31, and the inner push rod 33, the vial 1, and the piston rod 22 move forwards relative to the base 31 to compress the medicine liquid within the medicine liquid receiving chamber 215 via the piston rod 22, thereby completing injection. Specifically, the injection step further includes an unlocking step and a resilient actuation step.

If injection is required, the button 341 at the rear end of the base 31 is pressed to move forwards. In the case, the protrusion portion 341c at the front end of the button 341 moves forwards to release radial restriction on the limiting member 344 such that the limiting member 344 can move radially outwards to unlock the rear end 3351 (which is formed in a flange structure) of the transmission rod 335. In addition, along with the forward movement of the button 341, the inner push rod system 334 is driven to move forwards via the button spring 343 and the spring receiving portion. The transmission rod 335 passes over the limiting member 344, causing the locking mechanism 34 to unlock the inner push rod system 334.

After unlocking, the inner push rod system 334 can move forwards relative to the base 31. At this time, the pressurized actuation spring 36 applies a large thrust to the front end flange 331a of the inner push rod 33 such that the inner push rod 33 drives the piston rod 22 to move forwards to compress the medicine liquid within the medicine liquid receiving chamber 215 and thus eject the medicine liquid out of the injection micropore 211.

As can be seen from the above-mentioned steps, the front end flange 331a of the inner push rod 33 is provided for at least two purposes: one is that, at the pressurized energy accumulation step, a force is applied to the front end flange 331a of the inner push rod 33 when the outer housing 32 moves rearwards relative to the base 31, to drive the inner push rod 33 to move rearwards along therewith relative to the base 31 until reaching the locked position where the inner push rod 33 is locked by the locking mechanism 34; and the other is that, at the injection step, as being pressed between the base 31 and the front flange 331a of the inner push rod 33, the actuation spring applies a thrust to the front end flange 331a to push the inner push rod 33 forwards to complete injection.

Figure 28:
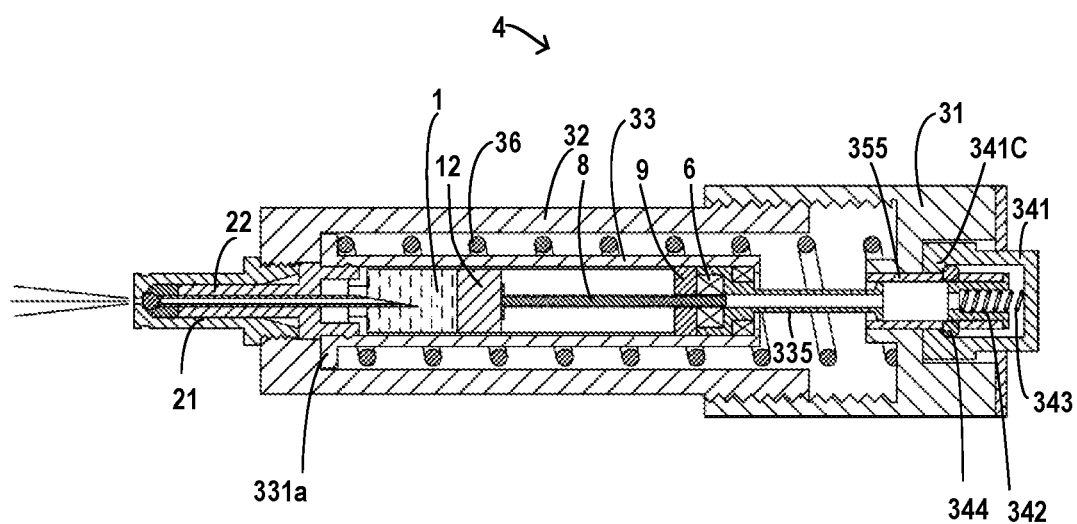
Figure 29:
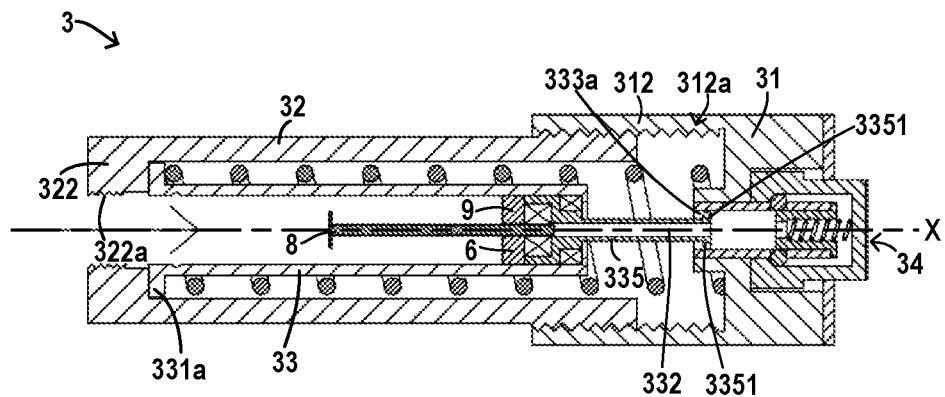
FIG. 29 is a section view of the needleless syringe body in FIGS. 22-28 after finishing needleless injection.

After one injection is completed, the vial 1 may not be removed for a next injection. In other words, the medicine liquid within the vial 1 may be provided for multiple injections. It would be appreciated that, after multiple injections, the cork 12 of the vial 1 will be continuously (which means continuously in space, rather than time) pushed forwards by the medicine supply push rod 8. FIGS. 28 and 29 illustrate the structure of the needleless syringe body after multiple injections.

In the circumstance, if pushed rearwards back to the initial position, the medicine supply push rod 8 may be rotated relative to the nut member 9. In order to accelerate the operation, the nut member 9 may be preferably configured to allow the medicine supply push rod 8 to directly move rearwards relative to the nut member 9 while not rotating relative to the latter.

To this end, the nut member 9 may be configured as at least two nut members separate from each other, which can move radially outwards in a specified condition, thereby disengaging from the medicine supply push rod 8. FIGS. 31-34B illustrate three examples.

In the examples as shown in FIGS. 31-34B, at least two nut members are arranged around the medicine supply push rod 8, and each can move radially towards or away from the axis to engage with or disengage from the medicine supply push rod 8.

Figure 31:
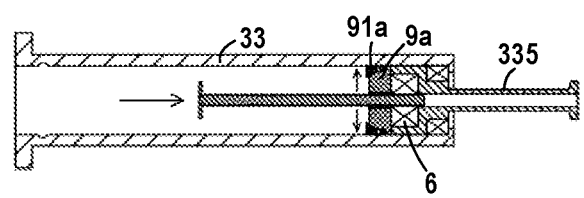
FIG. 31 is a section view of the structure in FIGS. 22-28 where an inner push rod system, a nut member and a one-way bearing are in an assembled state, according to an alternative embodiment.
Figure 32A:
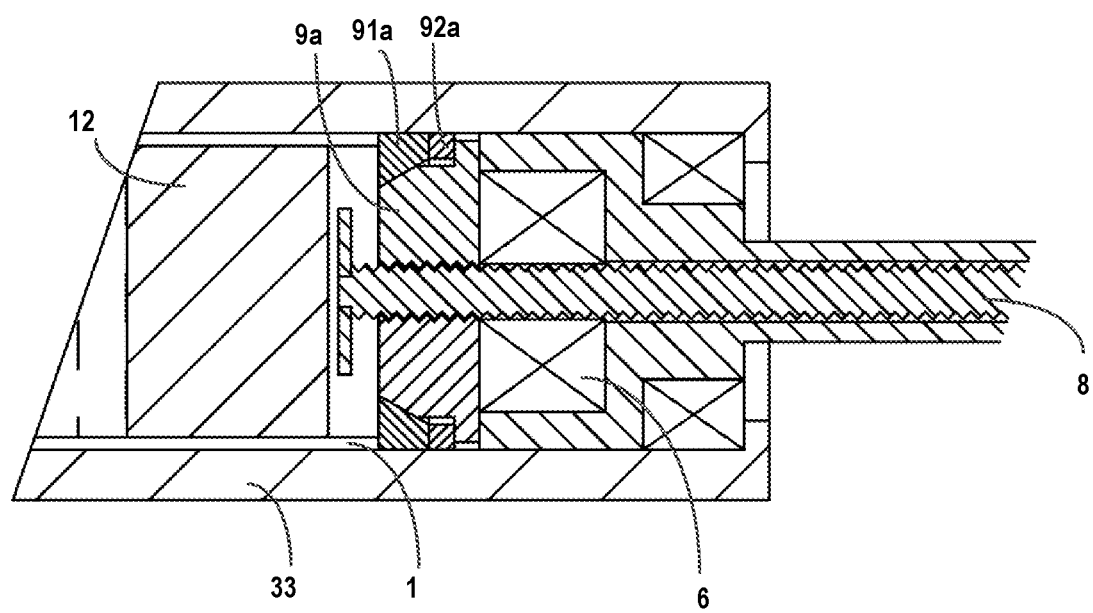
FIG. 32A is a schematic diagram of respective members in FIG. 31 when the nut member and a medicine supply push rod are in an engaged state.
Figure 32B:
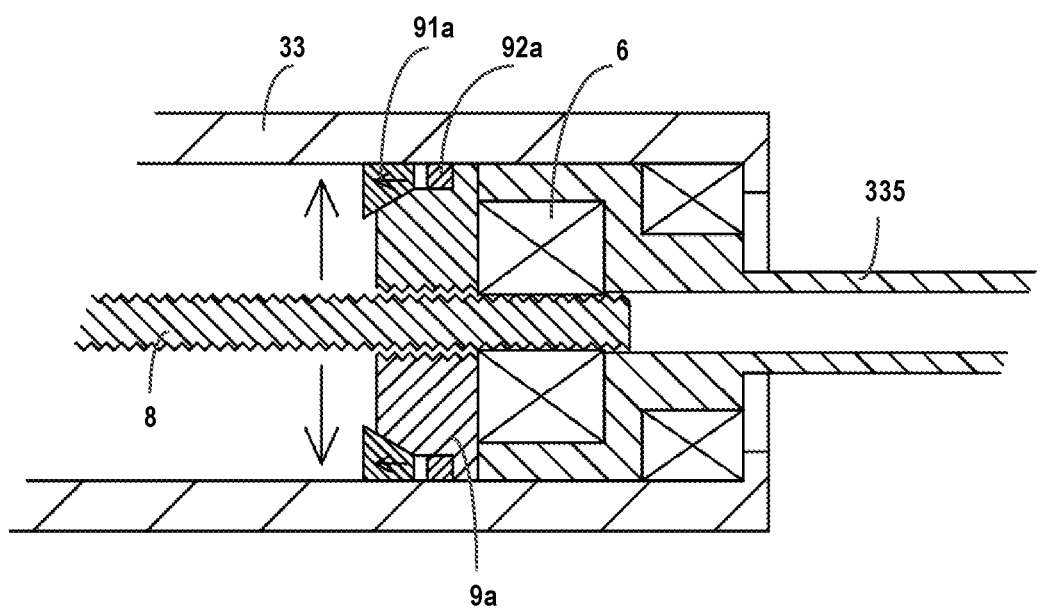
FIG. 32B is a schematic diagram of respective members in FIG. 31 when the nut member and the medicine supply push rod are in a disengaged stated.

In the example as shown in FIGS. 31-32B, there are two nut members 9a, each nut member 9a at the front end is provided with a nut limiting member 91a, and the surface of the nut member 9a contacting with the limiting member 91a is a force bearing slope. Wherein, the rear end of the force bearing slope is farther away from the axis X of the needleless syringe in the radial direction than the front end. The nut limiting member 91a is a wedge which has a force applying slope contacting with the force bearing slope.

As shown in FIG. 32A, when mounted within the needleless syringe, the vial 1 can press the nut limiting member 91a rearwards, and the nut limiting member 91a exerts a force to the force bearing slope of the nut member 9a. Since the pressure borne by the force bearing slope 9a is perpendicular to the slope, the pressure on the nut member 9a has an inward force component along the radial direction of the needleless syringe body, which presses the nut member 9a for engagement with the medicine supply push rod 8.

As shown in FIG. 32B, when the vial 1 is removed, the nut limiting member 91a slides forwards to reduce the pressure applied to the nut member 9a, such that the nut member 9a moves radially outwards to disengage from the medicine supply push rod 8. At this time, the medicine supply push rod 8 can be directly pushed back to an initial position.

Preferably, the nut limiting member 91*a* at the rear end is further provided with a second limiting member 92*a* to prevent a exceedingly long rearward movement distance of the nut limiting member 91*a* which may bring about an excessively large force applied to the nut member 9*a*.

Figure 33A:
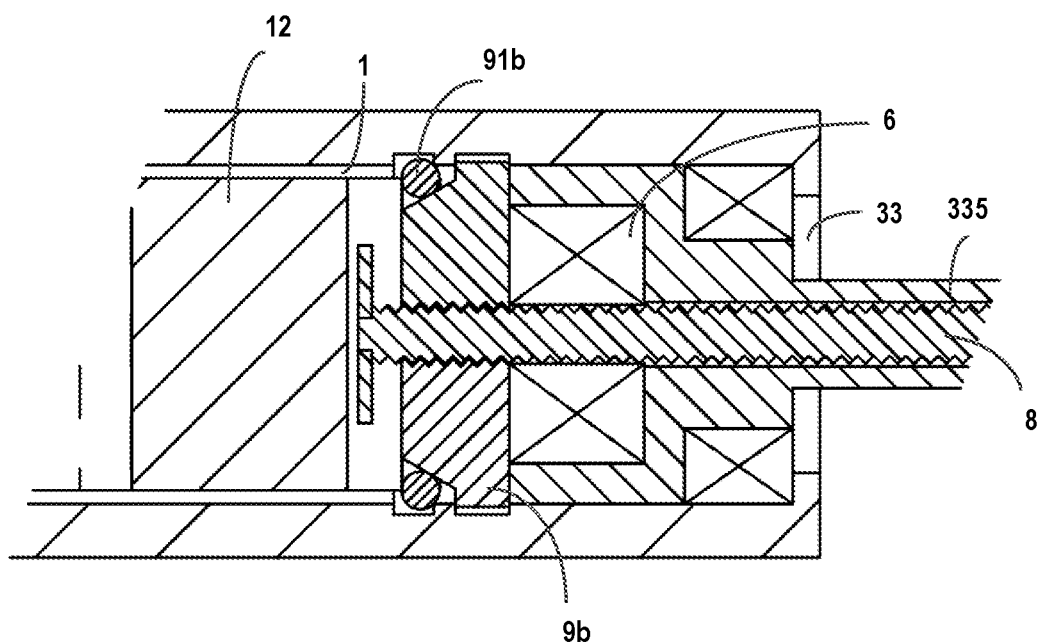
FIGS. 33A-33B are schematic diagrams of an alternative solution of FIGS. 32A-32B.
Figure 33B:
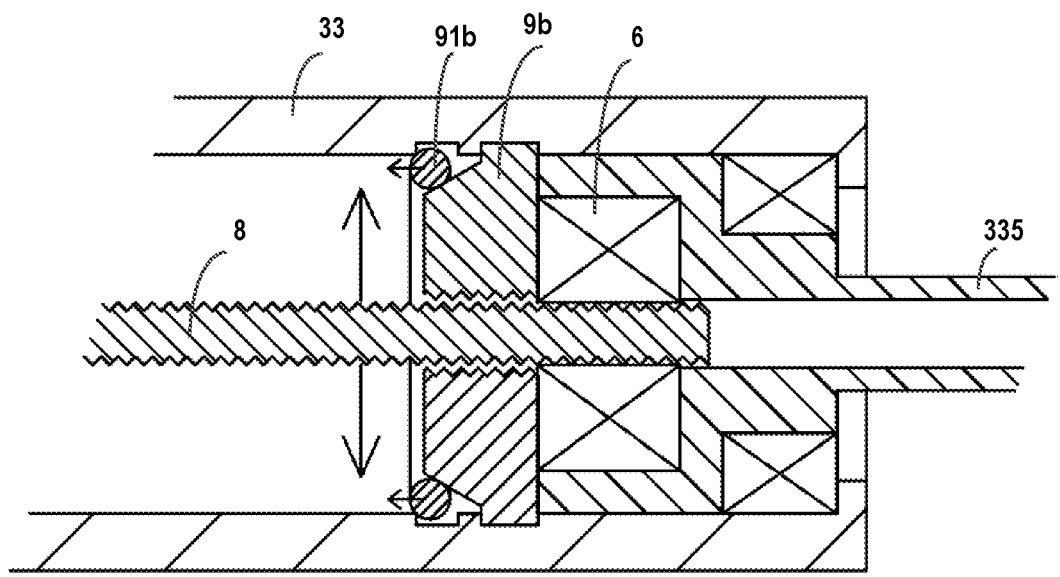

The example in FIGS. 33A and 33B is similar to the one in FIGS. 32A and 32B, but a nut limiting member 91*b* of an annular structure is used to replace to the wedge. The annular structure is coaxial with the needleless syringe body 3, and a section after it is cut by a plane where the axis X is located (for example, in FIGS. 33A and 33B) is circular. In the embodiment, the contact between the nut limiting member 91*b* and the nut member 9*b* is point contact.

In the state as shown in FIG. 33A, as pressed rearwards by the vial 1, the nut limiting member 91*b* compresses the nut member 9*b* into engagement with the medicine supply push rod 8. As shown in FIG. 33B, the vial 1 was removed, the nut limiting member moves forwards, and the nut member 9*b* moves radially outwards to disengage from the medicine supply push rod 8.

In addition, in embodiments not shown therein, the nut limiting member may be of a spherical structure, a sphere movement slot is provided correspondingly at a front end of a radial outer edge of the nut member, and the nut limiting member is limited within the sphere movement slot, making it impossible to escape therefrom.

Figure 34A:
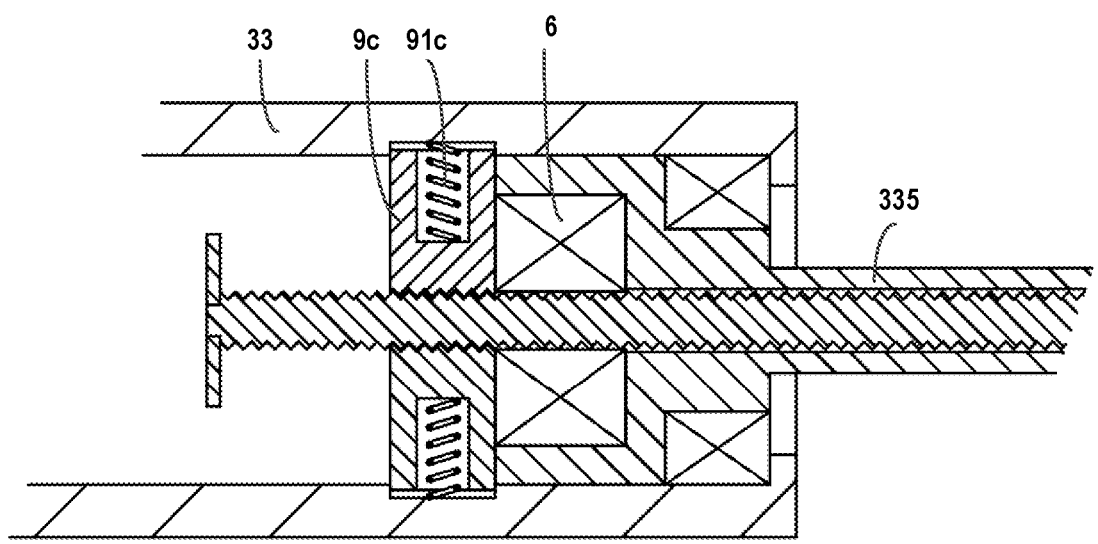
FIGS. 34A-34B are schematic diagrams of a further alternative solution of FIGS. 32A-32B.
Figure 34B:
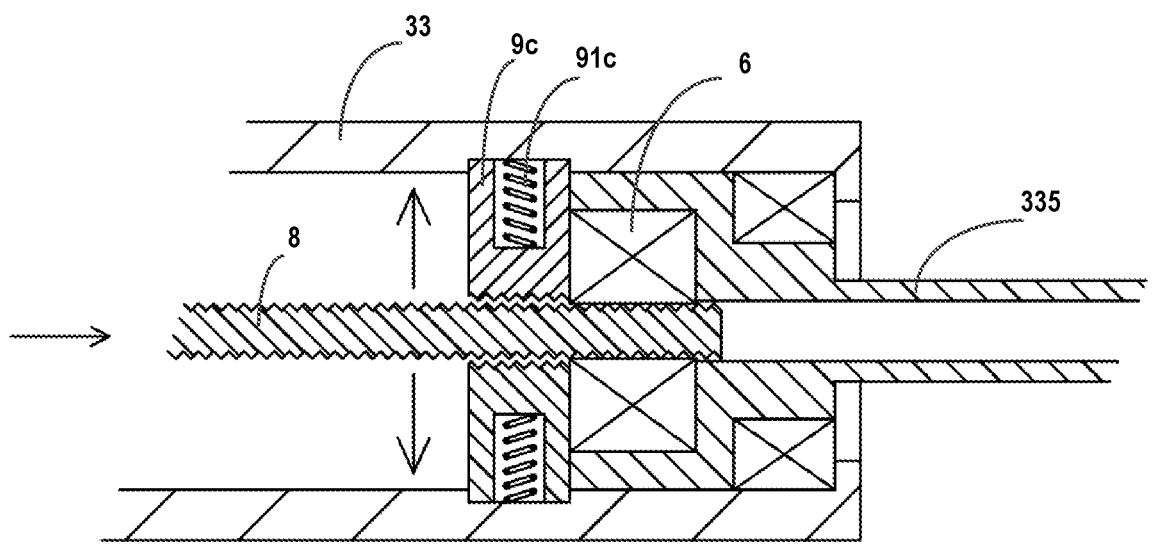

The structure as shown in FIGS. 34A and 34B is a more preferable structure. In the example, the medicine supply push rod 8 applies an axial force to the nut member 9*c* (i.e., the medicine supply push rod 8 has a tendency of moving axially relative to the nut member 9*c*, in case of not rotating relative to the same), and when the force reaches a predetermined threshold, the nut member 9*c* moves radially outwards, thereby not disengaging from the push rod.

In other words, when it is required to push the medicine supply push rod 8 back to the original position, only the medicine supply push rod 8 needs to be pushed, and the nut member 9*c* naturally moves radially outwards to permit axial translation of the medicine supply push rod 8.

Moreover, the medicine supply push rod 8 can be subjected to a forward thrust, in addition to the rearward force, and when the thrust reaches a predetermined threshold, the nut member 9*c* moves radially outwards to disengage from the medicine supply push rod 8. Specifically, the nut member 9*c* may disengage from the medicine supply push rod 8 in use when the thrust on the medicine supply push rod 8 is too great, thereby protecting the vial.

In connection with the injection head of the needleless syringe, the needleless syringe body, and the needleless syringe body assembly according to the present disclosure, the vial can be received within the needleless syringe body for a long time. And medicine suctioning and injection can be completed efficiently and effortlessly during each use, where there is no need for removing the vial or separating the medicine barrel from the vial. In the medicine suctioning process, the medicine supply push rod can push the cork forwards, so as to further improve the medicine suctioning efficiency. Furthermore, as the vial is received within the needleless syringe body, issues such as vial loss, contamination, and the like can be prevented.

Through the above disclosure, those skilled in the art would readily envisage using substitutes for the structures disclosed herein as feasible substitute embodiments, or combining the embodiments disclosed therein to form new embodiments. Such embodiments all fall into the scope claimed in the appended claims.

I claim:

1. A needleless syringe body for use with an injection head comprising a medicine barrel (21) and a piston rod (22) having a piston (221) and a rod portion (222), and a vial, characterized in that the needleless syringe body (3) comprises:
    a base (31) comprising a forward opening;
    an outer housing (32) comprising a rearward opening and mounted at a front end of the base to form a receiving space between the base and the outer housing, the outer housing being provided with a front opening for fixedly mounting a medicine barrel;
    an inner push rod (33) disposed within the receiving space and having a forward opening, the vial is fixedly received within the inner push rod, and the piston rod is configured to be fixed at the forward opening,
    wherein the outer housing can move in a front-rear direction relative to the inner push rod to drive the medicine barrel to move in the front-rear direction relative to the vial and the piston rod, so as to implement medicine suctioning and injection.

2. The needleless syringe body according to claim 1, characterized in that the needleless syringe body further comprises a locking mechanism (34) connected between the base and the inner push rod, and the locking mechanism is configured to lock the inner push rod (33) relative to the base (31) during medicine suction, and unlock the inner push rod (33) after medicine suction to cause the inner push rod (33) to move forwards relative to the outer housing (32).

3. The needleless syringe body according to claim 2, characterized in that the inner push rod at a rear end is provided with a rear end flange (333) protruding radially outwards, and the locking mechanism comprises:
    a limiting member (34) configured to abut against a front end face of the rear end flange in a locked state to limit forward movement of the inner push rod;
    a button (341) mounted on a rear end wall of the base and protruding rearwards relative to the base,
    wherein the button is configured to be pushed to move forward relative to the base and apply directly or indirectly a thrust to a rear end face of the inner push rod, and the rear end flange of the inner push rod can pass over the limiting member under an action of the thrust, causing the locking mechanism to unlock the inner push rod.

4. The needleless syringe body according to claim 3, characterized in that the locking mechanism further comprises:
    a spring receiving member (342) disposed between the rear end face of the inner push rod and a rear end wall of the button and having a spring receiving chamber opening rearwards;
    a button spring (343) disposed in the spring receiving chamber and configured to contact with the button at its rear end;
    wherein the button can be pushed to indirectly apply a thrust to the inner push rod via the button spring and the spring receiving member.

5. The needleless syringe body according to claim 3, characterized in that the button has a rear end wall, and a sidewall extending forwards from the rear end wall around an axis of the needleless syringe body, the sidewall at a front end is provided with a protrusion portion (341*c*) protruding towards the axis, and the limiting member is configured to move relative to the button in a radial direction relative to the axis, wherein, in the locked state, the protrusion portion abuts against a radial outside of the limiting member to limit radial outward movement thereof, the protrusion portion moves forwards relative to the limiting member when the button is pushed, to release radial restrictions thereon, and at this time the limiting member can move radially outwards to disengage from the front end face of the rear end flange, thereby unlocking the inner push rod.

6. The needleless syringe body according to claim 5, characterized in that the limiting member is a sphere, and a rear end face (341d) of the protrusion portion and a front end face (333a) of the rear end flange are slopes, such that the limiting member can be in rolling contact with the slopes during unlocking.

7. The needleless syringe body according to claim 2, characterized in that the locking mechanism is an electromagnet.

8. The needleless syringe body according to claim 1, characterized by further comprising a resilient actuation mechanism disposed between the base and the inner push rod, which is configured to be operated before injection for energy accumulation, and to be released after energy accumulation to actuate the inner push rod forwards via a resilient force to complete injection.

9. The needleless syringe body according to claim 8, characterized in that the inner push rod is provided with a front end flange (331a) at an inner end for protruding radially outwards, and the resilient actuation mechanism comprises an actuation spring (36) disposed between the front end flange and the base.

10. The needleless syringe body according to claim 9, characterized in that the base comprises a rear end portion and a base sidewall (312), the base sidewall at an inner surface is provided with internal threads (312a), the outer housing at a rear outer surface is provided with external threads corresponding to the internal threads, and cooperation of the internal threads and the external threads enables the outer housing to move rearwards relative to the base, thereby stably compressing the actuation spring.

11. A needleless syringe (4), comprising the needleless syringe body according to claim 1 and the injection head for use with the needleless syringe body.

12. A needleless syringe body for use with an injection head and a vial, the vial comprising a vial body having a vial receiving chamber, and a cork slidable within the vial receiving chamber in a front-rear direction relative to the vial body, the injection head comprising a medicine barrel (21) and a piston rod (22) having a piston (221) and a rod portion (222), characterized in that the needleless syringe body (3) comprises:
a base (31) having a forward opening;
an outer housing (32) having a rearward opening and mounted at a front end of the base to form a receiving space between the base and the outer housing, the outer housing provided with a front opening for fixedly mounting a medicine barrel;
an inner push rod system (334) comprising an inner push rod (33) disposed within the receiving space and having a forward opening, the vial is fixedly received within the inner push rod, and the piston rod is configured to be fixed at the forward opening;
a medicine supply push rod (8) mounted at a rear end of the inner push rod, the medicine supply push rod at a front end being in contact with the cork of the vial; and
a transmission, wherein a part of the transmission is connected to the medicine supply push rod (8) while the other part thereof is directly or indirectly connected to the base (31) or the outer housing (32),
wherein the outer housing can move in a front-rear direction relative to the inner push rod, to drive the medicine barrel to move in the front-rear direction relative to the vial and the piston rod, to implement medicine suctioning and injection, and
wherein, in a medicine suctioning process, the base or the outer housing drives, via the transmission, the medicine supply push rod to move the cork of the vial forwards relative to the vial body, so as to compress a space within the vial.

13. The needleless syringe body according to claim 12, characterized by further comprising a locking mechanism (34) connected between the base (31) and the inner push rod system (334), which is configured to lock the inner push rod system during medicine suction to lock the inner push rod system in the front-rear direction relative to the base (31), and to unlock the inner push rod system after medicine suction to move forwards relative to the outer housing (32).

14. The needleless syringe body according to claim 13, characterized in that the base (31) and the outer housing (32) are engaged and being rotatable relative to each other, such that, through relative rotation between the outer housing (32) and the base (31), relative movement of the outer housing (32) and the base (31) can be achieved in an axis direction of the needleless syringe body.

15. The needleless syringe body according to claim 14, characterized in that the inner push rod system (334) further comprises a transmission rod (335) which is connected to the transmission at a front end and engaged with the locking mechanism at a rear end, and the transmission rod is fixed relative to the base in a rotational direction relative to the base when locked by the locking mechanism.

16. The needleless syringe body according to claim 15, characterized in that the transmission comprises transmission for rotational movement which is configured to transmit specified rotational movement of the transmission rod (335) to the medicine supply push rod (8) to drive the medicine supply push rod (8) to rotate; and
further in that the needleless syringe body is provided with a movement conversion mechanism therein, and a part of the movement conversion mechanism is engaged with the medicine supply push rod (8) while the other part of the movement conversion mechanism is directly or indirectly engaged with the inner push rod (33) to convert rotational movement of the medicine supply push rod (8) along with the transmission rod (335) into linear movement of the inner push rod (33).

17. The needleless syringe body according to claim 16, characterized in that, in the medicine suctioning process, the outer housing (32) rotates relative to the base (31) to move forwards relative to the same; and
the transmission for rotational movement comprises a one-way transmission for rotational movement which is configured to transmit the rotational movement of the transmission rod (335) to the medicine supply push rod (8) when the outer housing (32) rotates relative to the base (31) to move forwards relative to the base, and to stop transmitting the rotational movement of the transmission rod to the medicine supply push rod when the outer housing (32) rotates relative to the base (31) to move rearwards relative to the same.

18. The needleless syringe body according to claim 17, characterized in that the one-way transmission for rotational movement comprises a one-way bearing (6), which is fixedly connected at an outer ring (61) to the transmission rod (335), and fixedly connected at an inner ring (62) to the medicine supply push rod (8) in a rotational direction about the axis of the needleless syringe body.

19. The needleless syringe body according to claim 16, characterized in that the movement conversion mechanism comprises a nut member (9) received in a receiving space of the inner push rod (33) and fixedly connected to the inner push rod, and the medicine supply push rod (8) is engaged with the nut member (9) by thread fit.

20. The needleless syringe body according to claim 19, characterized in that the nut member comprises at least two nut members separated from each other, which are arranged around the medicine supply push rod and can move towards or away from the axis of the needleless syringe body in a radial direction of the needleless syringe body, so as to engage with or disengage from the medicine supply push rod.

21. The needleless syringe body according to claim 20, characterized in that the at least two nut members (9c) are configured to move radially in a direction away from the axis and thus disengage from the medicine supply push rod, when the medicine supply push rod (8) applies a force to the nut members (9c) in an axial direction of the needleless syringe body and the force reaches a predetermined threshold.

22. The needleless syringe body according to claim 20, characterized in that the needleless syringe body further comprises a nut limiting member (91a, 91b) at a front end of each of the nut members (9a, 9b), wherein a surface of the nut member contacting with the nut limiting member is a force bearing slope, a rear end of the force bearing slope is radially farther away from the axis of the needleless syringe than a front end thereof, and the nut limiting member is configured to urge the force bearing slope rearwards to press the nut member into engagement with the medicine supply push rod, and to cause the nut member to move radially away from the other and thus disengage from the medicine supply push rod when stopping applying the force to the nut member.

23. The needleless syringe body according to claim 22, characterized in that the front end of the nut limiting member can be in direct contact with a rear end of the vial body, to press the nut member continuously as an effect of a rearward force of the vial body when the vial is mounted within the inner push rod, and the nut limiting member stops applying the force to the nut limiting member after the vial is removed from the inner push rod.

24. A needleless syringe (4), comprising the needleless syringe body according to claim 12 and an injection head for use with the needleless syringe body, the injection head comprising a medicine barrel (21) and a piston rod (22) having a piston (221) and a rod portion (222).

* * * * *